United States Patent [19]

Han et al.

[11] Patent Number: 5,244,662

[45] Date of Patent: Sep. 14, 1993

[54] MEDICINAL EXTRACT FROM A MIXTURE OF PHELLODENDRON AND DEFATTED SEED OF CROTON, AND METHOD FOR IT'S MANUFACTURE

[75] Inventors: Young B. Han; Hong K. Kyung; Jung J. Moon; Choon W. Kim; In G. Han; Jong B. Kim, all of Seoul, Rep. of Korea

[73] Assignee: Korea Green Cross Corporation, Kyongki, Rep. of Korea

[21] Appl. No.: 791,833

[22] Filed: Nov. 14, 1991

[30] Foreign Application Priority Data

Dec. 4, 1990 [KR] Rep. of Korea ............... 19896/1990

[51] Int. Cl.$^5$ .............................................. A61K 35/78
[52] U.S. Cl. .................................................. 424/195.1
[58] Field of Search ...................................... 424/195.1

[56] References Cited

PUBLICATIONS

Chem. Abst. Kondo, et al., 115(9):849836, 1991.
Chem. Abst. Moon, et al., 100:132269n, 1984.
C. K. Moon, et al., Arch. Phar. Res. 6(2):123–31, 1983.

*Primary Examiner*—John W. Rollins
*Attorney, Agent, or Firm*—Jordan and Hamburg

[57] ABSTRACT

An extract is derived from a mixture of the bark of the genus Phellodendron and the defatted seed of the genus Croton and has excellent therapeutic activity in treating various disorders of the immune system. The extract is obtained by extracting the mixture with an organic solvent, filtering the resulting mixture to separate a residue, extracting the residue with hot water to obtain a water soluble solution, concentrating the solution under reduced pressure and saturating vapor pressure, and removing the resulting precipitates from the solution. If necessary, the obtained solution is again extracted with an organic solvent, the resulting organic solvent and water soluble layers separated, and the water soluble layer purified and lyophilized to obtain a yellowish brown powder which can be used as the effective ingredient in a pharmaceutical composition for treating a wide range of immune system disorders.

8 Claims, 18 Drawing Sheets

(1)

(2)

(3)

(4)

(1)

(2)

(3)

(4)

MEDICINAL EXTRACT FROM A MIXTURE OF PHELLODENDRON AND DEFATTED SEED OF CROTON, AND METHOD FOR IT'S MANUFACTURE

BACKGROUND OF THE INVENTION

The present invention relates to novel compositions of matter having excellent activity with respect to cancers, tumours, thyroid disorders, etc., which are extracted from a mixture of the bark of the genus Phellodendron and the defatted seed of the genus Croton, a method for extraction therefor and a drug containing the same.

Cancers, tumours, etc., are the result of immune disorders and have become a social problem in any society whose members have a prolonged life-span. Development of medicines useful for treating or preventing these diseases is thus desired.

Many medicines and reports thereon have revealed numerous ways of treating these diseases, but they suffer from the disadvantage that they attack normal cells as well as abnormal cells. Therefore, even if the patient recovers from the cancer, tumour, etc., they almost cannot survive due to the toxicity of the medicine. Accordingly, development of a medicine capable of improving the immune system without producing any subsidiary ill effects has been desired.

SUMMARY OF THE INVENTION

The present inventors conducted intensive studies for improving the general immune system during treating of cancers, tumours, etc., and found that the extract from a mixture of the bark of the genus Phellodendron and the defatted seed of the genus Croton has excellent activity as to disorders of the immune system. Such a finding has led to the completion of the present invention.

The genus Phellodendron is native to Korea, Japan, China, etc. It includes Phellodendron amurense ruprecht, Latifoliolatum nakai ex Kawamoto, Japonicum ohwi, Phellodendron insulare nakai, Phellodendron molle nakai, Phellodendron sachalinence sargent, etc. The bark contains yellow and yellowish brown pigments, and a few alkaloids which have been known, in the art, to have a complex range of therapeutic activities, antibacterial, antihypertensive, antiinflammatory, and acetylcholine-stimulating activities, etc., and also to be effective for treatment of jaundice and some bone diseases.

Plants of the genus Croton are leafy shrubs native to Southeast Asia, and include Croton tiglium L, Jatropha curcas L, Codiaeum variegatum blum, Pictum muell, etc. Among them, Croton tiglium L has been used to treat cancers, tumours, etc., from the time of Hippocrates. However, Croton oil, which is obtained by extraction, is toxic to humans and is known to be carcinogenic (cf. Cancer Research 28, pp. 2338–2339, November 1968). Therefore, the seed of Croton has heretofore hardly been used as a drug.

Thus, a purpose of the present invention is to provide an extract having therapeutic actions against neoplastic and related diseases.

Another object of the present invention is to provide a drug or pharmaceutical composition comprising an effective amount of the extract.

Yet another object of the present invention is to provide a method for extraction.

The extract according to the present invention is effective for the treatment of the following diseases and symptoms:

Neoplasm

The antineoplastic activity of the extract according to the present invention affects the metabolic systems of tumour cells. It blocks and/or inhibits the pathway of essential amino acids of the tumour to suppress cellular growth. It also plays a significant role in increasing the defense mechanism of the host so that tumour cells may shrink, be reduced, and then diminished by enhancing the homeostatic function and by activating the controlling power of the immune system, neuroendocrinological system and the enzyme-substrate-level of the host.

Viral disease

The extract according to the present invention exerts antiviral activity by improving immuno-deficiency of a host through enhancement of T-lymphocyte functions. The extract of the present invention produces helper factors, activates macrophages to release interleukin I(IL-I) which acts during antigen priming of lymphocytes, stimulates T-lymphocytes to release interleukin II(IL-II) which is essential for long term growth of T-cell helper and consequently results in enhancement of T-cell functions.

Thyroid disease

The extract of the present invention exerts a therapeutic activity for thyroid diseases by restoring to normal the homeostasis mechanism of the thyroidal gland and also thyroidal hormone secretion. It activates the suppressor T-lymphocytes(Ts) of the immune system and restores to normal the homeostatic deficiency of thyroid, as well as the Ts-lymphocyte function affecting thyroid cells. The present extract converts the Ts-lymphocyte to a typical lymphocyte(plasma cell) and reduces the development of antigen when the cell is overstimulated. Therefore, it exerts a similar effect on the normalized secretion of thyroid hormone. The present extract also regulates thyrotropin and restores to normal thyroid hormone secretion.

Osteoporosis

The extract of the present invention is effective for the treatment of osteoporosis by enhancing bone matrix synthesis and density. It increases estrogen and calcitonin secretion and decreases thyrotropin, which are all closely related to bone metabolism.

Liver disease

The present extract activates immunological and endocrinological functions and enhances the regenerative change of liver cells. The present extract restores a series of liver functions, improving GOT/GPT, albumin, globulin and bilirubin titers by activatinq the liver immune system. It increases TsF and enhances the Ts-lymphocyte function but suppresses the functions of Th-lymphocyte, Tc-lymphocyte and Te-lymphocyte.

The present extract also restores to normal the hormonal functions involved in glucose metabolism. It increases glucose levels in hypoglycaemia cases, and thus is effective for maintaining glucose levels within a normal range.

BRIEF DESCRIPTION OF THE DRAWINGS

Various features and advantages of the present invention will become more readily apparent from the following description, taken in conjunction with the accompanying drawings, in which.

DESCRIPTION OF THE PREFERRED EMBODIMENTS

Figure 1:
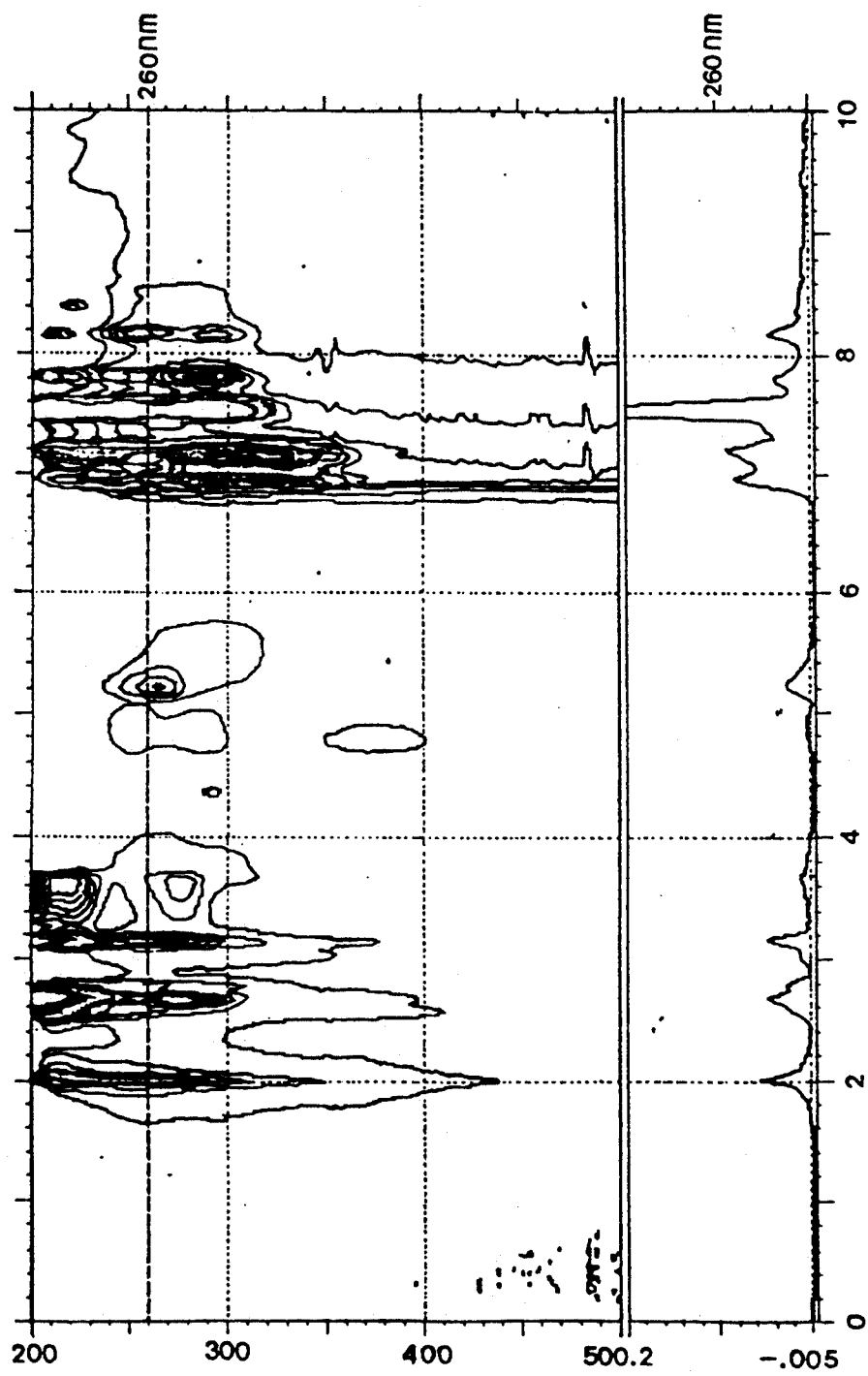
FIG. 1 represents an HPLC spectrum of the extract obtained in Example 1.
Figure 2:
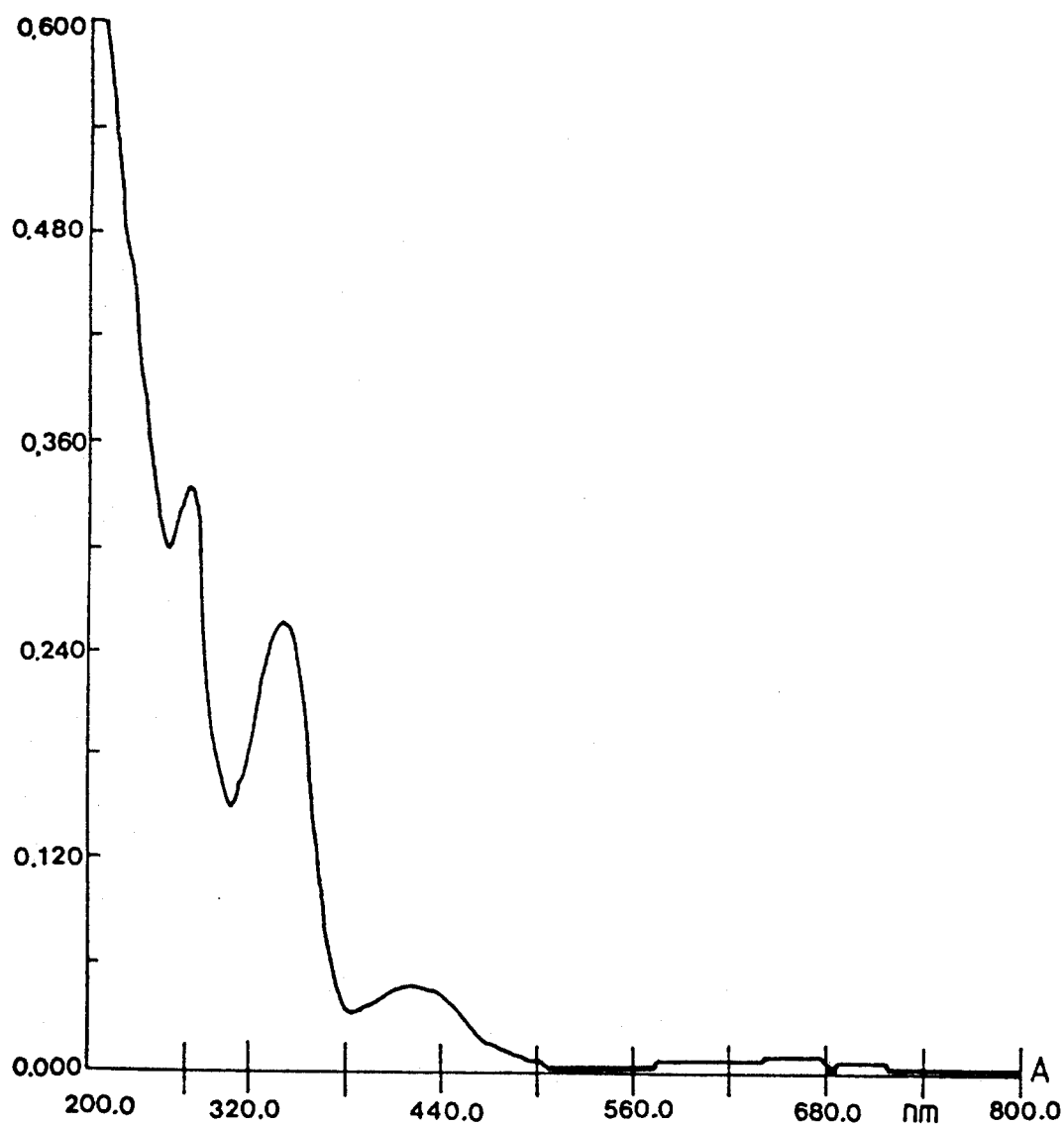
FIG. 2 represents a UV spectrum of the extract obtained in Example 1.
Figure 3:
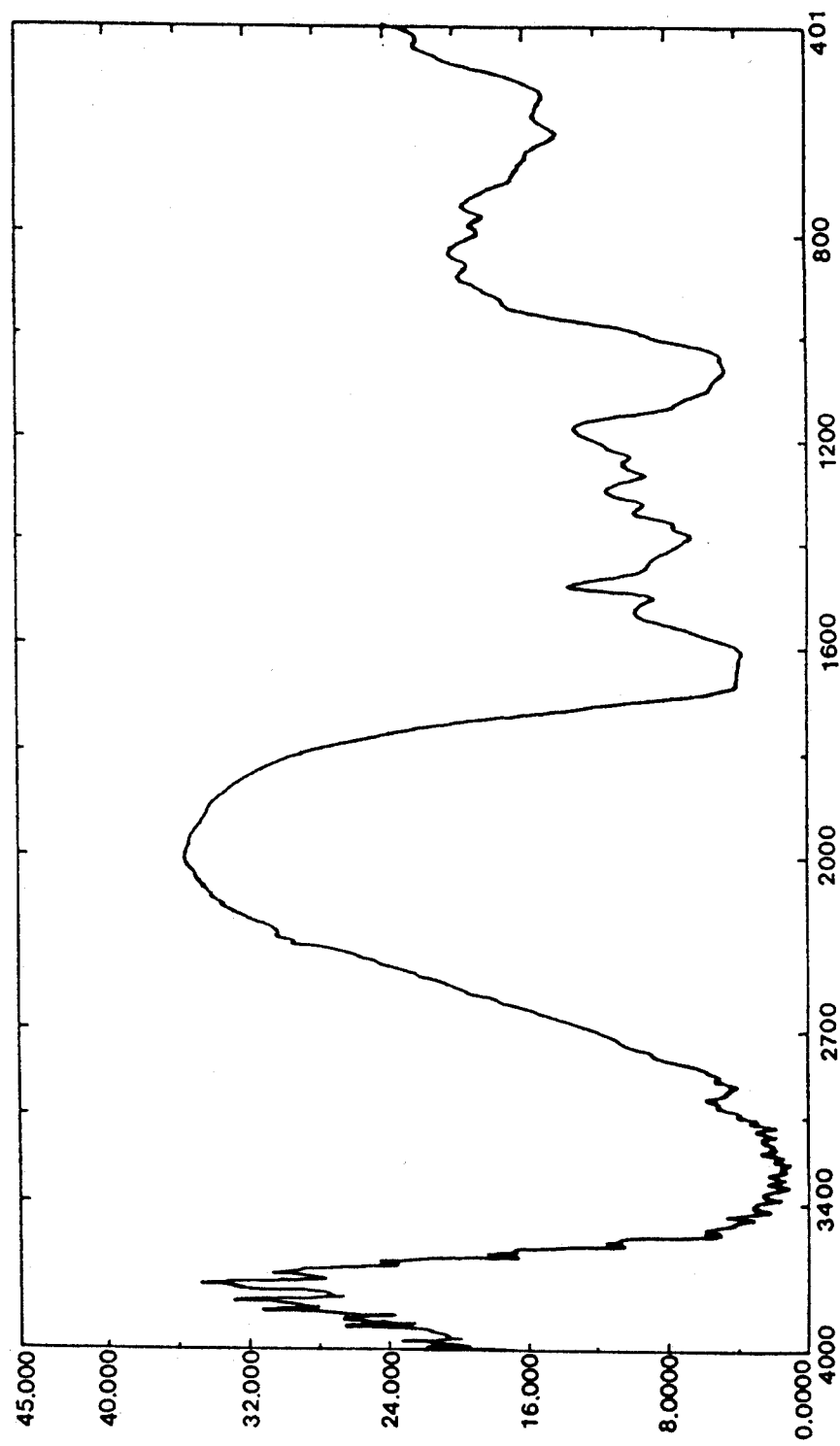
FIG. 3 represents an IR spectrum of the extract of Example 1.
Figure 4:
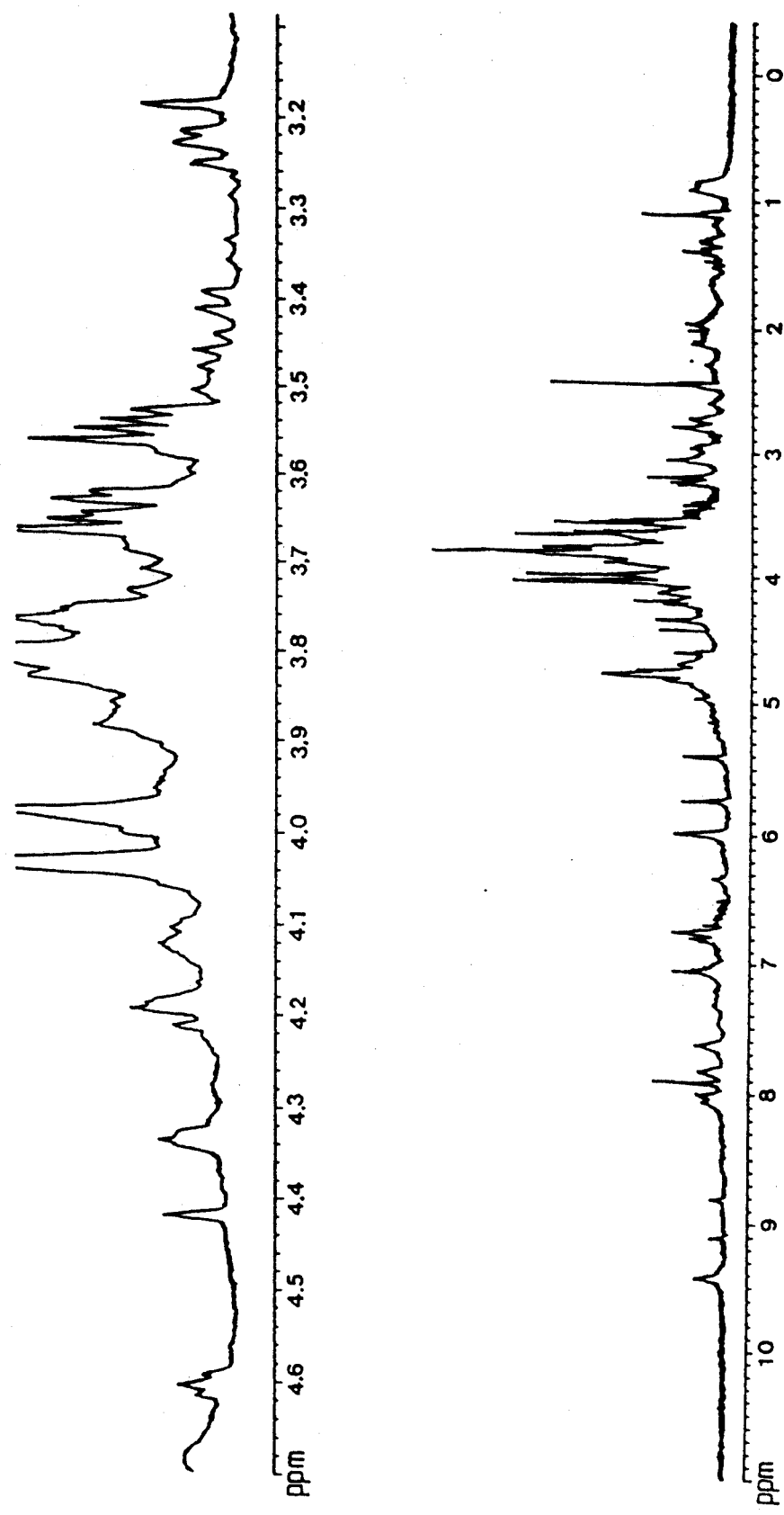
FIG. 4 represents an NMR spectrum of the extract of Example 1.

The extract of the present invention can be obtained by extracting a mixture of the bark of the genus Phellodendron and the defatted seed of the genus Croton with an organic solvent such as an aliphatic or aromatic alcohol, a halogenated hydrocarbon having 1-6 halogen atoms, or a carboxylic ester having a lower alkyl group. Preferably, chloroform, or a mixture of chloroform and ethanol, is used at a temperature of from room temperature to 50° C. for 20 to 60 hours, followed by filtering the resulting mixture to obtain a residue, extracting the residue with hot water to obtain a water soluble solution, concentrating the solution under reduced pressure with saturating vapor pressure, and then removing the resulting precipitates from the solution. If necessary, the obtained solution may again be extracted with such a solvent to give a water soluble layer, which is then lyophilized to obtain a yellowish brown powder. The properties of the obtained powder are as follows:

1. Elementary Analysis::
C: 39–41%, H: 4–6%, O: 45–47%, N: 5–7%

2. HPLC analysis:
component A (retention time: 2.0 min) : 6–8%
component B (retention time: 2.8 min) : 6–8%
component C (retention time: 3.1 min) : 5–7%
component D (retention time: 5.2 min) : 5–7%
component E (retention time: 7.1 min) : 33–35%
component F (retention time: 7.5 min) : 33–35%
component G (retention time: 8.2 min) : 4–6%

3. UV(KBr):
339 nm (azo functional group)
262 nm (substituted benzene functional group)

The following examples illustrate a particular embodiment of the present invention, but the scope of the present invention is not limited thereby.

EXAMPLE 1

160 g of bark of Phellodendron amurense ruprecht and 160 g of defatted seed of Croton tiglium(L) were pulverized and the mixture was poured into 2000 ml of a mixture(1:1) of chloroform and ethanol. The mixture was stirred for 48 hours at room temperature. This procedure was repeated three times. The solvent, containing mainly triglyceride and oil soluble material, was discarded and the residue thus obtained dried under dry air to remove the solution completely.

The solid residue obtained above was extracted four times with 1000 ml of distilled hot water at 60° C. The extract obtained was concentrated to ⅓ volume under reduced pressure and further saturated with vapor pressure (120° C., 20 pounds/cm$^2$), and then centrifuged to separate and remove precipitates. Chloroform was added to the residual solution and separated. This procedure was repeated several times. A water soluble extract was obtained and transferred to another distillatory apparatus to remove the organic solvent completely.

The water soluble extract was purified by adding talc and then filtered out under reduced pressure. The purified water soluble extract was filtered through a membrane filter (diameter: 142 mm; pore size: 0.2 μm) to remove bacteria and lyophilized to obtain about 20 g of pale yellowish brown powder. The properties thereof are as follows, and HPLC, UV spectrum, IR spectrum and NMR spectrum are shown in FIGS. 1 to 4, respectively.

1 Elementary analysis::
C: 39-85%, H: 4.62%, O: 47.04%, N: 5-24%, S: 0%
2. HPLC analysis:
component A (retention time: 2.0 min) : 7.1%
component B (retention time: 2.8 min) : 7.1%
component C (retention time: 3.1 min) : 6.2%
component D (retention time: 5.2 min) : 6.5%
component E (retention time: 7.1 min) : 33.6%
component F (retention time: 7.5 min) : 33.6%
component G (retention time: 8.2 min) : 5.8%
3. UV(KBr):
339 nm (azo functional group)

262 nm (substituted benzene functional group)
4. IR spectrum($cm^{-1}$) : 576, 1301, 1237, 1152, 1509, 1607, 3459, 2926, 3328

The powder thus obtained was dissolved in distilled water to pH 6.0 and formulated as an injectable solution for testing.

EXAMPLE 2

160 g of bark of Phellodendron sachalinence sargent and 160 g of defatted seed of Croton tiglium(L) were incised into small pieces. The mixture was stirred in 2000 ml of benzyl acetate for 36 hours at room temperature. This process was repeated three times. The solution was discarded and the remaining mixture was dried under an air blow to remove the solution completely.

The solid residue thus obtained was extracted four times, each time with 1000 ml of hot water at 60° C. The extract obtained was concentrated under reduced pressure to ⅓ volume and then saturated with vapor pressure (120° C., 20 pounds/cm²). The mixture was centrifuged to separate out the precipitates. To the residual solution, chloroform was added and the organic layer was separated out. This procedure was repeated several times. A water soluble extract was obtained and transferred to another distillatory apparatus to remove the organic solvent completely.

The water soluble extract was purified by adding talc and then filtered out under reduced pressure. The purified water soluble extract was filtered through a membrane filter (diameter: 142 mm, pore size: 0.2 μm) to remove bacteria and lyophilized to obtain about 18 g of pale yellowish brown powder. The properties thereof are as follows:
1. Elementary analysis:
C: 39.28%, H: 4.83%, O: 47.22%, N: 5.42%, S: 0%
2. HPLC analysis:
component A (retention time: 2.0 min) : 6.9%
component B (retention time: 2.8 min) : 6.9%
component C (retention time: 3.1 min) : 6.0%
component D (retention time: 5.2 min) : 6.1%
component E (retention time: 7.1 min) : 34.6%
component F (retention time: 7.5 min) : 34.1%
component G (retention time: 8.2 min) : 5.3%
3. UV(KBr):
339 nm (azo functional group)
262 nm (substituted benzene functional group)
4. IR spectrum($cm^{-1}$) : 576, 1301, 1237, 1152, 1509, 1607, 3459, 2926, 3328

The powder thus obtained was prepared into an injectable solution using the same procedure as in Example 1.

EXAMPLE 3

160 g of bark of Phellodendron insulare nakai and 160 g of defatted seed of Croton tiglium(L) were incised into small pieces. The mixture was stirred in 2000 ml of chloroform for 24 hours at room temperature. This process was repeated three times. The solution was discarded and the remaining mixture was dried under an air blow to remove the solution completely. The solid residue thus obtained was extracted four times, each time with 3000 ml of hot water at 90° C. The extract obtained was concentrated under reduced pressure to ⅓ volume and then saturated with vapor pressure (120° C., 20 pounds/cm²). The mixture was centrifuged to separate out the precipitates. To the residual solution, chloroform was added and the organic layer was separated out. This procedure was repeated several times. A water soluble extract was obtained and transferred to another distillatory apparatus to remove the organic solvent completely.

The water soluble extract was purified by adding talc and then filtered out under reduced pressure. The purified water soluble extract was filtered through a membrane filter (diameter: 142 mm, pore size: 0.2 μm) to remove bacteria and lyophilized to obtain about 20 g of pale yellowish brown powder. The properties thereof are as follows:
1. Elementary analysis::
C: 39.85%, H: 4.62%, O: 47.04%, N: 5.24%, S: 0%
2. HPLC analysis:
component A (retention time: 2.0 min) : 6.8%
component B (retention time: 2.8 min) : 6.8%
component C (retention time: 3.1 min) : 6.1%
component D (retention time: 5.2 min) : 6.4%
component E (retention time: 7.1 min) : 34.5%
component F (retention time: 7.5 min) : 34.5%
component G (retention time: 8.2 min) : 4.8%
3. UV(KBr :
339 nm (azo functional group)
262 nm (substituted benzene functional group)
4. IR spectrum($cm^{-1}$) : 576, 1301, 1237, 1152, 1509, 1607, 3459, 2926, 3328

EXAMPLE 4

Pharmacological Action of the Extract

The pharmacological action of the extract of the present invention was tested using the extract obtained from Example 1.

(A) $LD_{50}$ of the present extract was determined according to the Korea National Institute of Health Standard and Behrens-Carber method.

Male ddy mice (weight 17±1g) were used as subjects. Test extracts were administered, starting with 435 mg/KG and increased step-by-step to 705 mg/Kg for ip/im, and 125 mg/Kg to 285 mg/Kg for iv. $LD_{50}$ was determined after 7 days from starting administration to give the following results:

$LD_{50}$ ip/im = 655 mg/Kg $LD_{50}$ iv = 250 mg/Kg (B) Haematological and pathological tests were carried out by administering 100 to 400 mg/Kg of the extract obtained from Example 1 to ddy mice (weight: about 20 g) by ip.

The blood in the heart was removed and the femurs were cut out from the mice and haematological findings and tissular change of bone marrow, respectively, were observed. The results are shown in Table 1. The key organs were observed for pathological tests, and the results thereof shown in Table 2.

The present extract showed no significant changes in blood, bone marrow and key organs at a dose of 100 to 400 mg/Kg.

TABLE 1

Haematological observation on mice

| treatment (mg/Kg) | RBC $10^4 mm^3$ | WBC $mm^3$ | Hb g/dl | MCV $\mu^3$ | MCH $\mu\mu g$ | MCHC % | PLT $mm^3$ |
| --- | --- | --- | --- | --- | --- | --- | --- |
| control | 665 | 6200 | 12.4 | 53 | 19.3 | 35.1 | 130,000 |
| 100 | 774 | 7000 | 14.9 | 57.6 | 19.2 | 33.4 | 121,000 |
| 150 | 792 | 6400 | 15.3 | 51.6 | 19.4 | 37.5 | 140,000 |
| 200 | 573 | 6200 | 11.3 | 53.2 | 19.4 | 36.4 | 112,000 |
| 300 | 523 | 5600 | 11.1 | 53.3 | 19.4 | 37.8 | 127,000 |
| 400 | 520 | 5650 | 10.2 | 53.1 | 19.2 | 36.1 | 136,000 |

| treatment (mg/kg) | Ret. | Lymph | Hemogram (%) Mono count | Seg | Eosine | Morphology WBC | RBC | Hct | Rdw | bone marrow |
| --- | --- | --- | --- | --- | --- | --- | --- | --- | --- | --- |
| control | 3.3 | 77 | 3.0 | 17 | 3 | NR | NR | 35.8 | 9.6 | NR |
| 100 | 3.2 | 77 | 3.1 | 17 | 2 | NR | NR | 44.6 | 11.4 | NR |
| 150 | 3.3 | 76 | 3.0 | 17 | 4 | NR | NR | 44.9 | 9.1 | NR |
| 200 | 3.1 | 77 | 3.0 | 17 | 3 | NR | NR | 31.1 | 8.7 | NR |
| 300 | 3.3 | 77 | 3.0 | 17 | 3 | NR | NR | 35.2 | 8.4 | NR |
| 400 | 3.2 | 77 | 3.0 | 17 | 3 | NR | NR | 33.8 | 8.5 | NR |

*NR: normal

TABLE 2

Pathological Observation on mice

| Treatment (mg/Kg) | Liver | Kidney | Heart | Brain |
| --- | --- | --- | --- | --- |
| control | Kupercell, liver cell portal v. central v. Normal | Glomerulus Tibule Normal | Myocardium and blood vessels Normal | cell and blood vessel of large/small brain Normal |
| 100 | same as above | same as above | same as above | same as above |
| 200 | same as above | same as above | same as above | same as above |
| 300 | same as above | same as above | same as above | same as above |
| 400 | same as above | same as above | same as above | same as above |

| Treatment (mg/Kg) | Spleen | Lungs | Stomach | (Reproductive) Testicles | Thyroid Gland |
| --- | --- | --- | --- | --- | --- |
| Control | W. pulp R. pulp Normal | Alveolar Vessel Normal | Mucous Muscle Normal | Sperm production physical change Normal | Epithelial cell and thyroxin secretion Normal |
| 100 | same as above | same as above | same as above | same as above | same as above |
| 200 | same as above | same as above | same as above | same as above | same as above |
| 300 | same as above | same as above | same as above | same as above | same as above |
| 400 | same as above | same as above | same as above | same as above | same as above |

(C) Effects of the basic experiment on tumour cells

Myeloma is a cell which has been used for cell nuclear fission purposes when producing a monoclone antibody. Since it has characteristics of the common tumour cells, it is generally selected as an experimental cell to examine the inhibiting effects of drugs against the proliferation of tumour cells.

The activity of the present extract against the proliferation of Myeloma and Granuloma cells metastasized with tumour cells, Lymphoma and normal cells were as follows:

(C-1) Actions on Myeloma bone marrow tumour cells

Myeloma cells of mouse Sp s/0-Ag(ATCC : CRL 1581), $2.5 \times 10^4$ cells, were inoculated in 1 ml of complete culture medium at 37° C./10%/$CO_2$ for cultivation as a control.

Figure 25:
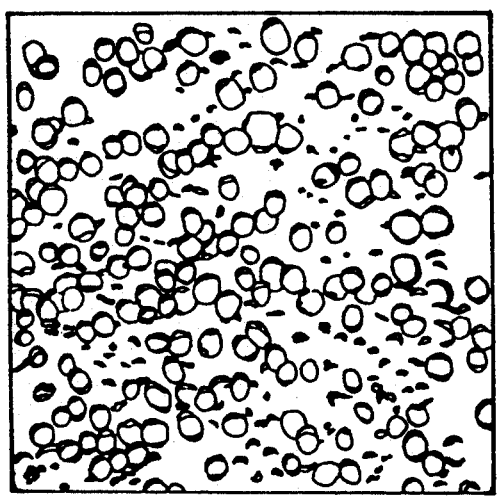
FIG. 25 represents sketchy drawings of antitumour activity against myeloma, in which FIG. 25(1) is the cell morphology for the control, FIG. 25(2) is the cell morphology for a 0.25 mg/ml dose regimen, FIG. 25(3) is the cell morphology for a 1.0 mg/ml dose regimen and FIG. 25(4) is the cell morphology for a 2.5 mg/ml dose regimen.
Figure 25:
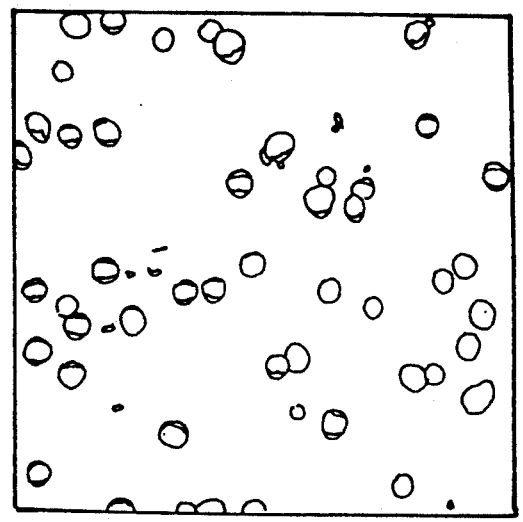
Figure 25:
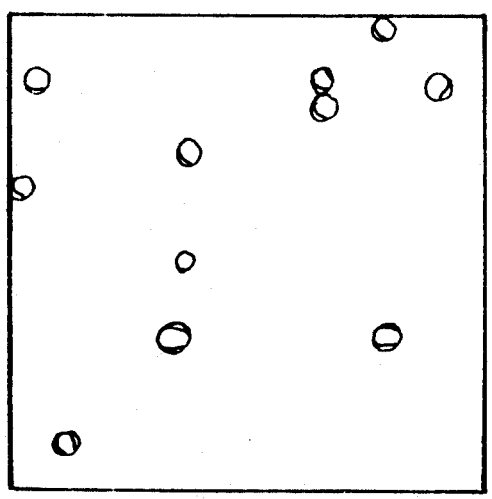
Figure 25:
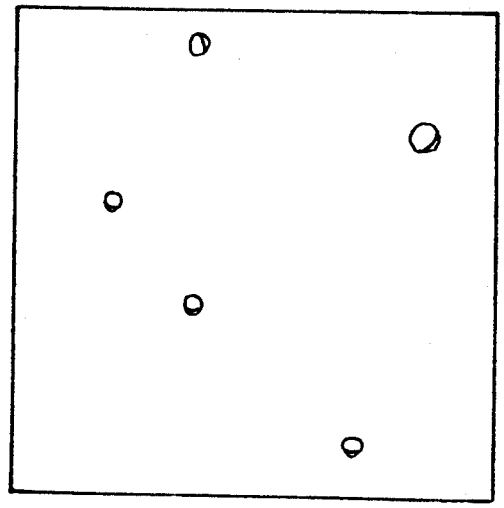

The same number of Myeloma cells were inoculated in 1 ml of culture medium treated with the present extract, 0, 0.5, 1.0, 2.5 mg each, and cultured. FIGS. 25(1) to 25(4) show the results of microscopic observations of the cells cultured for 48 hours.

More remarkable decreases were observed in a number of the cells in the test group containing the present invention. More particularly, in the medium containing 2.5 mg/ml of the present extract, a proliferation-inhibiting effect was observed to such an extent that few living tumour cells were found.

(C-2) Actions on Granuloma cells metastasized with Oncogene SV-40 and Ha-Ras

Granuloma cells play an important role in producing ovum in mammalian animals, and particularly secrete progesterone to enhance the proliferation of ovum. Granuloma cells metastasized artificially with carcinogenic genes (SV-40 and Ha-Ras) have the ability to synthesize both progesterone, the cell's original function and protein, and the original function of the carcinogenic gene. For the test, PO-GRSI and PA-GS6 were cultured in DMEM/F12(1:1) haematologic culture media containing insulin(2 $\mu g/ml$), transferin (5 $\mu g/ml$), hydrocortisone(40 $\mu g/ml$) and fibronectin(5 $\mu g/ml$), and the progesterone was analyzed by radioimmunoassay (TIA).

i) Actions on proliferation of PO-GRSI and PA-GS6

PO-GRSI and PA-GS6 cells were inoculated in a petri dish and cultured for 48 hours in culture media treated with 0.5 ml and 0.1 mg/ml of the extract obtained in Example 1, respectively. The proliferation-inhibiting figures were then calculated by investigating the survived cell numbers. As shown in Table 3, the survival numbers were reduced by 31.6% in a 0.25 mg/ml group for PA-GS6. It was more effective against PA-GS6. Similar proliferation-inhibiting figures were also obtained by calculating the protein concentration as shown in Table 4.

A high proliferation-inhibiting activity of the present extract against tumour cells was determined by comparing the proliferation-inhibiting figures for the two kinds of cells.

TABLE 3

Proliferation-inhibiting activity of the extract against tumour cells

| cell | dose | No. of cells | growth rate (%) |
|---|---|---|---|
| PO-GRSI | control | 475 ± 6 | 100 |
|  | 0.25 mg/ml | 325 ± 25 | 68.6 |
|  | 1.0 mg/ml | 109 ± 1 | 22.6 |
| PA-GS6 | control | 460 ± 10 | 100 |
|  | 0.25 mg/ml | 215 ± 25 | 46.7 |
|  | 1.0 mg/ml | 23 ± 2 | 5.0 |

TABLE 4

Effect on quantity of protein by the present extract on cancer cells

| cell | dose | quantity of protein | growth rate (%) |
|---|---|---|---|
| PO-GRSI | control | 1117 ± 53 | 100 |
|  | 0.25 mg/ml | 767 ± 21 | 68.6 |
|  | 1.0 mg/ml | 388 ± 28 | 34.7 |
| PA-GS6 | control | 833 ± 48 | 100 |
|  | 0.25 mg/ml | 353 ± 92 | 42.3 |
|  | 1.0 mg/ml | 171 ± 15 | 20.5 |

(ii) Action on the steroid hormone synthesis of PO-GRSI and PA-GS6

The antitumour activities of the extract obtained in Example 1 against Granuloma cells were determined also by evaluating its action on the progesterone and 20 alpha —OH— progesterone synthesis of the captioned two kinds of cells. In the meantime, the action of FORSKOLIN to enhance the two steroid hormone syntheses were also checked.

As to PO-GRSI, the FORSKOLIN group showed a 100 times increase of 20 alpha-OH-progesterone synthesis and a 60 times increase of progesterone synthesis over the control group. The present extract group showed just a 1.3 times increase of progesterone synthesis and no difference in 20 alpha—OH—progesterone synthesis. Similar results were also obtained for PA-GS6.

It was determined that the present extract had little action on progesterone synthesis. As a result, it can be assumed that the effects of the present extract against the proliferation of neoplastic cells are not obtained through action on progesterone.

Table 5 shows the action of the present extract on progesterone and 20 alpha—OH—progesterone synthesis.

TABLE 5

Effects of the present extract on progesterone and 20 alpha-OH-progesterone

| cell | treatment | dose | progesterone (ng/ml) | 20 alpha-O progesterone (ng/ml) |
|---|---|---|---|---|
| PO-GRSI | control |  | 0.936 | 0.625 |
|  | extract | 0.25 mg/ml | 0.620 | 0.915 |
|  | extract | 1.0 mg/ml | 1.220 | 62.90 |
|  | forskoline | 10 |  |  |
| PA-GS6 | control |  | 0.521 | 0.713 |
|  | extract | 0.25 mg/ml | 0.694 | 0.736 |
|  | extract | 1.0 mg/ml | 1.280 | 0.734 |

Figure 26:
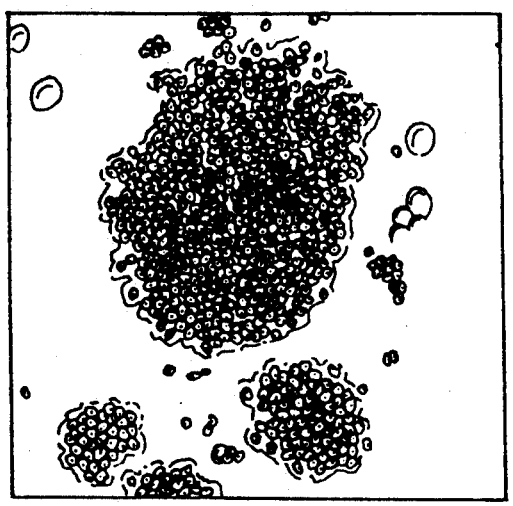
FIG. 26 represents sketchy drawings of the dispersion effect against lymphoma, in which FIG. 26(1) is the cell morphology for the control, FIG. 26(2) is the cell morphology for a 0.625 mg/ml dose, FIG. 26(3) is the cell morphology for a 1.25 mg/ml dose and FIG. 26(4) is the cell morphology for a 2.5 mg/ml dose.
Figure 26:
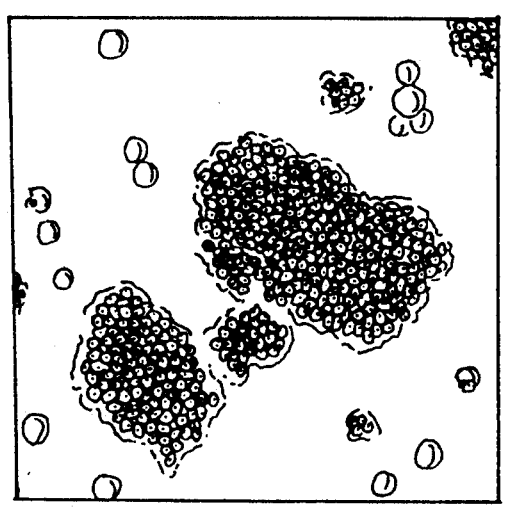
Figure 26:
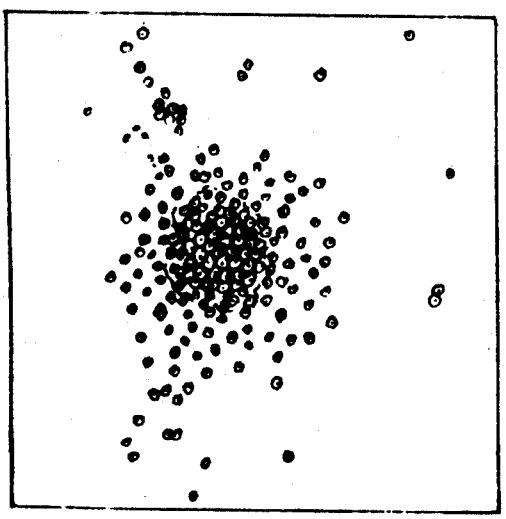
Figure 26:
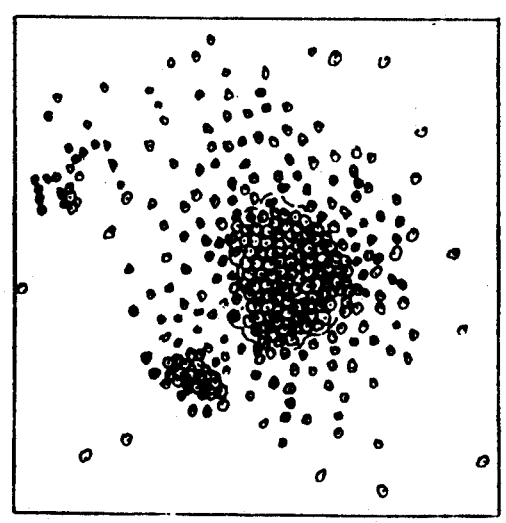

(C-3) Actions on the Proliferation of Lymphoma using Raji cells obtained from Texas University U.S.A. have been investigated Such cells were inoculated in the culture media RPMI-1640 supplemented with 10% fetal bovine serum. To the media, 0.625 mg, 1.25 mg, and 2.5 mg of the present extract was added, respectively, and the cells were cultured for 36 hours at 37° C. The results of the cells are shown in FIGS. 26(1) to 26(4).

A lymphoma cell is characterized by the formation of a proliferating colony on a culture media. The colony was dispersed in the test group at first and then it was diminished with time. It was determined that the proliferation of Raji cells, the lymphoma tumour cell, was markedly inhibited by the present extract.

(C-4) Action on normal cells

Current antitumour drugs affect normal cellular growth as well as growth of tumour cells, whereby very careful therapeutic application of the agents has been required. The development of more effective drugs affecting only tumour cells has been strongly required. The action of the present extract on spleen cells and granuloma cells was investigated to evaluate the action on normal cellular growth.

The spleen cells originated from BALB/C mice and were cultured in RPMI media under the condition of 7% $CO_2$/37° C. The granuloma cells originated from the ovum of young rats aged 25 days and were cultured in DMEM/F 12(1:1) media containing fetal bovine serum under the same conditions.

(i) Actions on spleen cells

Spleen cells were cultured for four days in culture media to which was added 2.5 mg/ml of the present extract. No difference was found in both the morphological findings and the survival number of cells.

Figure 27:
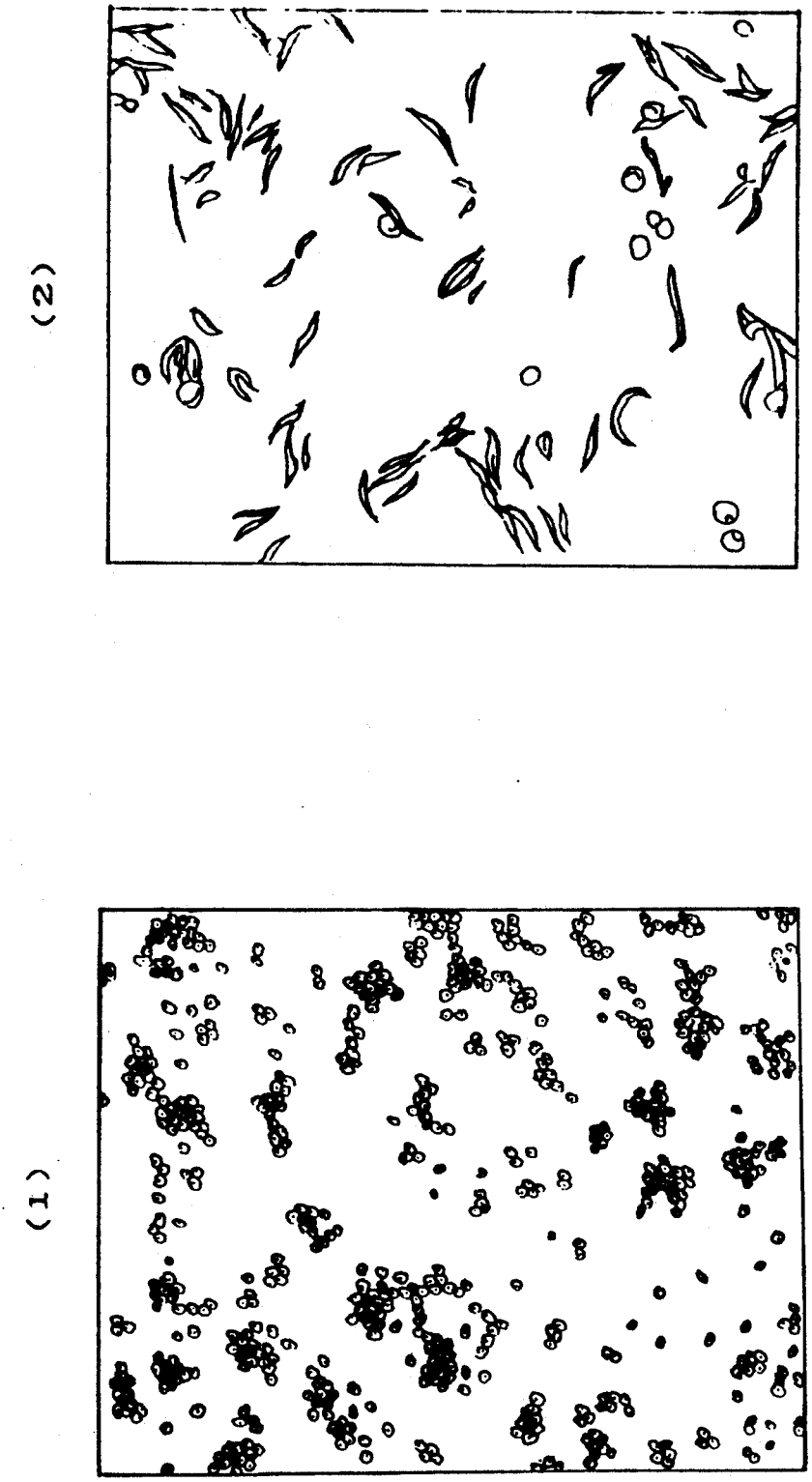
FIG. 27 represents sketch drawings of the morphology of spleen cells after a 2 week treatment, in which FIG. 27(1) is the morphological change for the control and FIG. 27(2) is the morphological change for a 2.5 mg/ml dose regimen.

After 14 days, significant morphological changes were observed in the cells of the control group but no change in the test group, as shown in FIGS. 27(1) and 27(2).

Considering the general difficulty in culturing spleen cells for 10 days or more, the fact that there were no morphological changes even after 14 days demonstrates a protective action of the present extract on normal cellular growth.

ii) Actions on granuloma cells

Granuloma cultured in the culture media containing 0.25 mg/ml of the present extract secreted about twice as much progesterone as the control, but secretion in the media containing 1.0 mg/ml was lower. Meanwhile, progesterone secretion in the media containing forskolin was eight times that of the control but the secretion decreased, by contrast, in the media containing both forskolin and the present extract.

As shown in Table 6, the present extract was not involved in the steroid synthesis of granuloma cells but showed a somewhat dose-dependent effect. It was also determined by experiment using PO-GRSI and PA-GS6 that the present extract did not affect normal cellular growth. This is authenticated by the fact that any functional alteration of the cell can develop only when it is closely related with progesterone.

It is also noticeable that the effect of forskolin to enhance progesterone synthesis was offset by the morphological changes of cells which might have been observed in culture media without the present extract, but which was not developed in culture media containing it.

The present extract is expected to offer a synergistic combination with currently used antitumour drugs. The present extract by itself exerts an antitumour activity and offsets the untoward effects of other drugs on normal cellular growth.

TABLE 6

| cell | Action on progesterone production of primary granuloma cells | | |
|------|-----------|------|---------------------|
| | treatment | dose | progesterone (ng/ml) |
| Granu-loma cell | control | | 109.6 |
| | present extract | 0.25 mg/ml | 222.4 |
| | present extract | 1 mg/ml | 126.0 |
| | forskolin | $10^{-4}$ M | 829.0 |
| | forskolin + present extract | $10^{-4}$ M + 0.25 mg/ml | 267.6 |

(D) Experiments on the effect of the present extract

It is determined that the present extract exerts antineoplastic activities by enhancing the defense mechanism of the host as well as a direct attack on the tumour cells. Although the pharmacological action and mechanism are not as yet fully established, they appear to act dynamically as follows:

(i) Enhancement of host defense mechanism

IL-2 stimulated T-cell helper(Th) has the function of recognizing antigen and maintaining the proliferation of clones of Th-cells for normal immunoresponse of the host. In the neoplastic patient, the IL-1/IL-2 synthesis is decreased and the receptor of lymphocyte is also decreased due to the deficiency of T-cell helper factors. The present extract stimulates IL-1/IL-2 and activates the lymphocyte function when the host immune system cannot discriminate a foreign body (self and non-self) due to the suppressed immunological control mechanism which recognizes whether it is the tumour-specific-antigen or not. Thus, it helps the lymphocytes attack the tumour cell.

(ii) Direct attack on tumour cells

The present extract directly dissolves and destroys lipoprotein in the outer film of lysosome and releases dehydrogenase of lysosome, as well as inhibiting coagulation of the fibrin layer formed by the tumour cell, and consequently disturbs the feed-back routes between host and tumour cell. Tumour cells mass-release specific enzymes and form a fibrin layer which allows only the necessary substances to pass into the tumour cell from the host.

(iii) Protection of normal cells

The currently-used cancer chemotherapy has cell toxicity, such as, inhibition of epithelial cell disorganization and disturbance of bone marrow to interrupt leucocyte synthesis.

A synergistic effect is expected, very positively, when administering the present extract rationally together with cancer chemotherapy because it can protect normal cells against chemotherapy as well as directly destroy tumour cells.

The experiments of the effect of the present extract are as follows:

(D-I) $ED_{50}$ Spectrum test

An antitumour spectrum test was carried out through a dose-effect relationship based on experimental pharmacology on effectiveness and toxicity for the quantitative analysis.

Sarcoma 180, ATCC TIB66 (hereinafter referred to as "S-180") and Ehrlich-Letter Ascites Carcinoma ATCC CCL77 (hereinafter referred to as "EAC") were inoculated, $1 \times 10^7$ cells each, intrasubcutaneously through the inguinal region of ddy mice. The present extract was administered intraperitoneally after 24 hours and thereafter once a day for 60 days. The dosage ranged from 50 to 700 mg/Kg.

Figure 5:
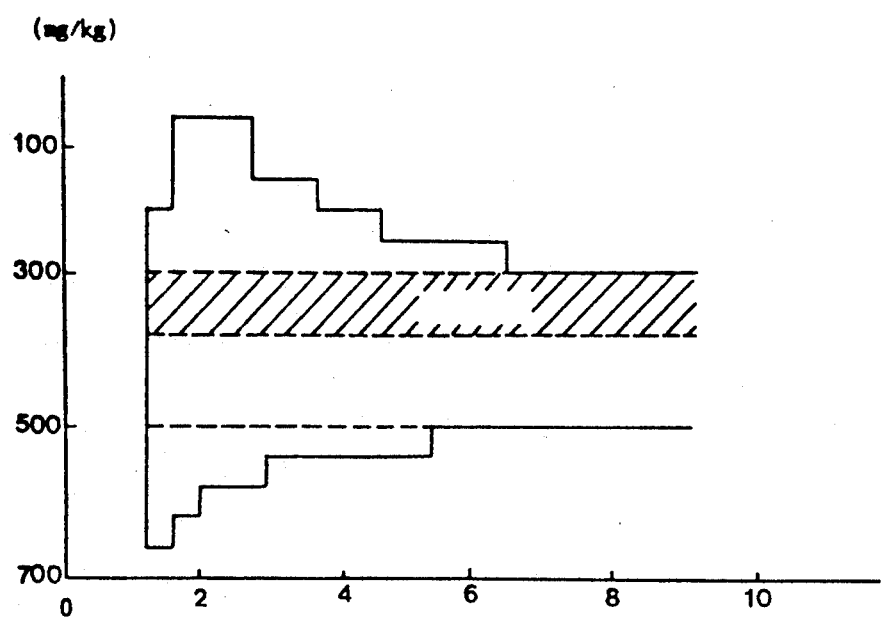
FIG. 5 represents an effectiveness-spectrum against S-180 and EAC nodular tumour.

As illustrated in FIG. 5 and Table 7, the present extract showed antitumour activities against the two solid tumour cells at the lowest dose of 200 mg/Kg. The maximum dose was 400 to 500 mg/Kg and optimum dose was 300 to 400 mg/Kg.

TABLE 7

Effect of the present extract in treatment of EAC Nodular Tumour

| dose (mg/Kg) | antitumour effects | prolonged life expectancy | optimum dose |
|------|------|------|------|
| 50 | + | − | |
| 100 | + | + | |
| 150 | ++ | + | |
| 200 | ++ | − | |
| 250 | ++ | ++ | |
| 300 | +++ | +++ | ** |
| 350 | +++ | +++ | ** |
| 400 | +++ | ++++ | ** |
| 450 | +++ | +++ | * |
| 500 | +++ | ++ | * |
| 550 | ++ | + | |
| 600 | + | − | |
| 650 | − | − | |
| 700 | − | − | | note)
+: 45%, ++: 65%, +++: 85%, ++++: 95%
*: effective dose, **: optimum dose (D-2) Antitumour effects against tumour S-180 and EAC were tested $1 \times 10^7$ cells of each of S-180 and EAC were inoculated intrasubcutaneously through the inguinal region of ddy mice. 400 mg/Kg of the present extract was administered intraperitoneally once a day for 60 days. The treatment started 24 hours for one group, and 7 days for another, after inoculation of the tumour cells.

Figure 6:
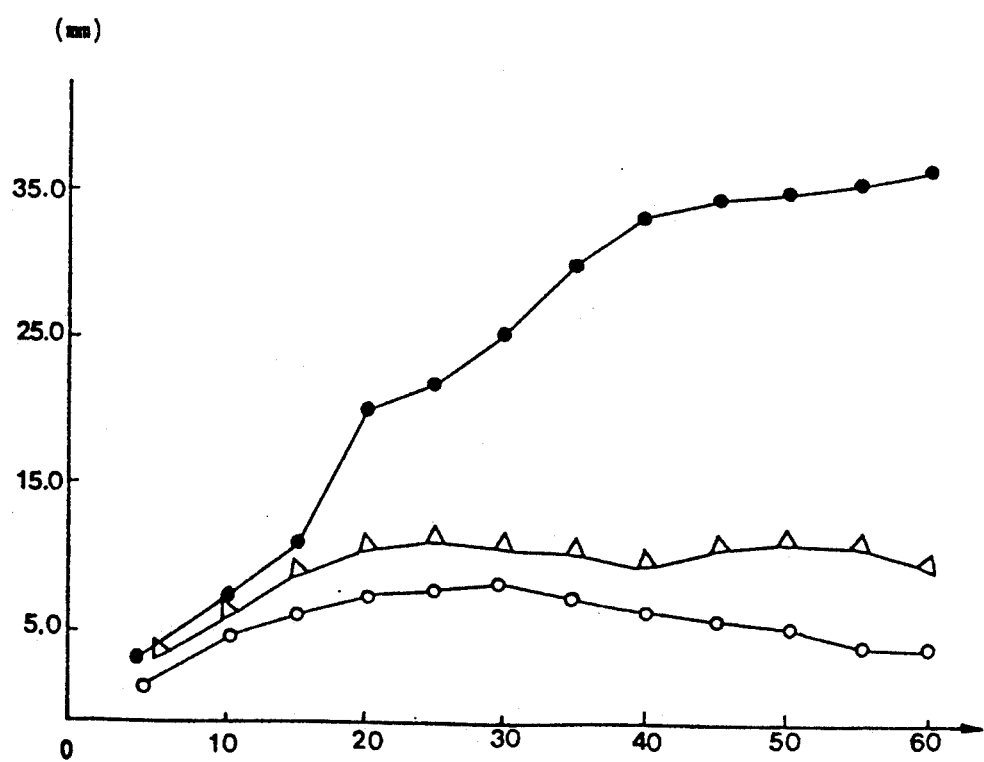
FIG. 6 shows the effect on diameter change of EAC nodular tumour.
Figure 7:
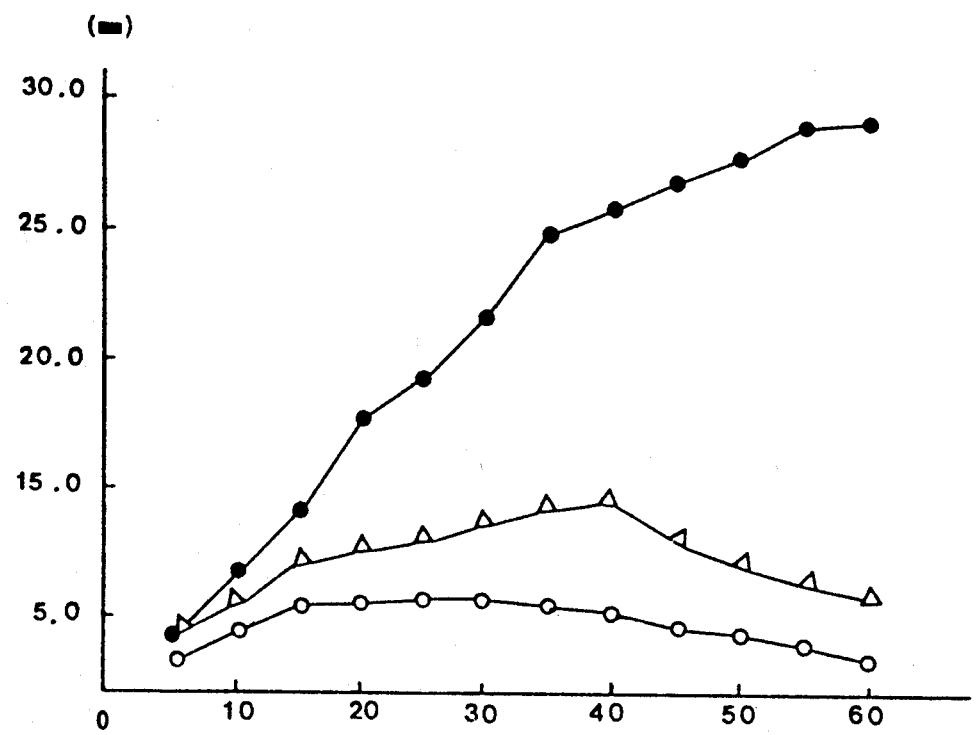
FIG. 7 shows the effect on diameter change of S-180 nodular tumour.

As shown in FIGS. 6 to 13, the control group died from tumour, but the tumour cells were reduced and diminished 30 days after inoculation in the test group. As shown in FIGS. 6 and 7, the diameter of a tumour cell after 60 days was 35 mm for the control group, but below 5 mm in the test group.

Figure 8:
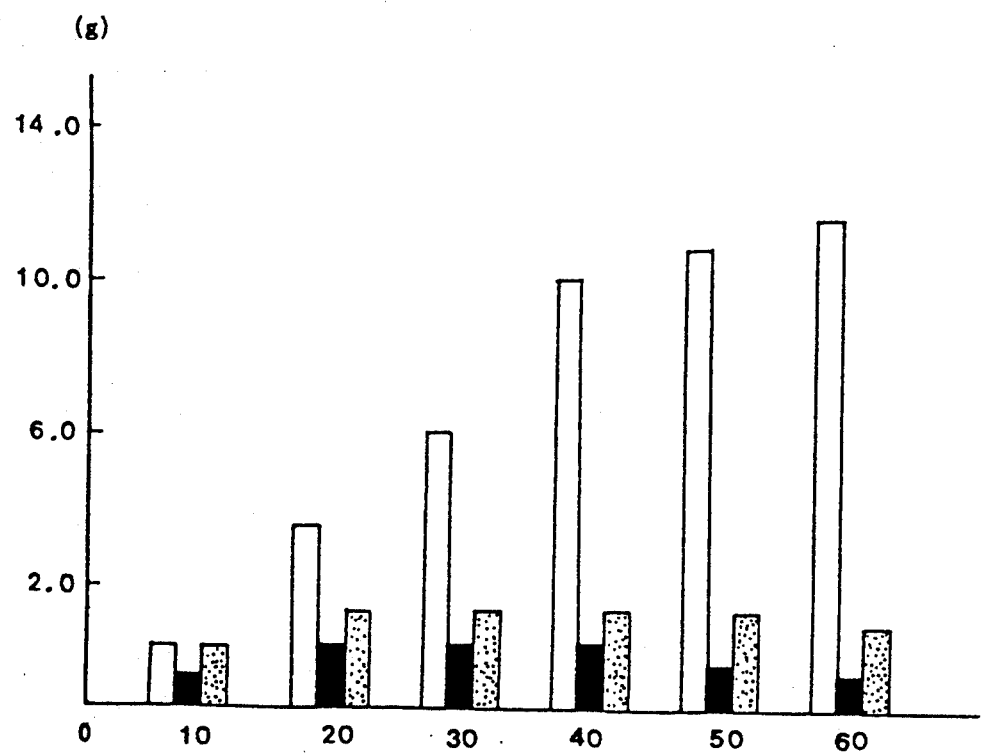
FIG. 8 shows the effect on weight change of the EAC nodular tumour.
Figure 9:
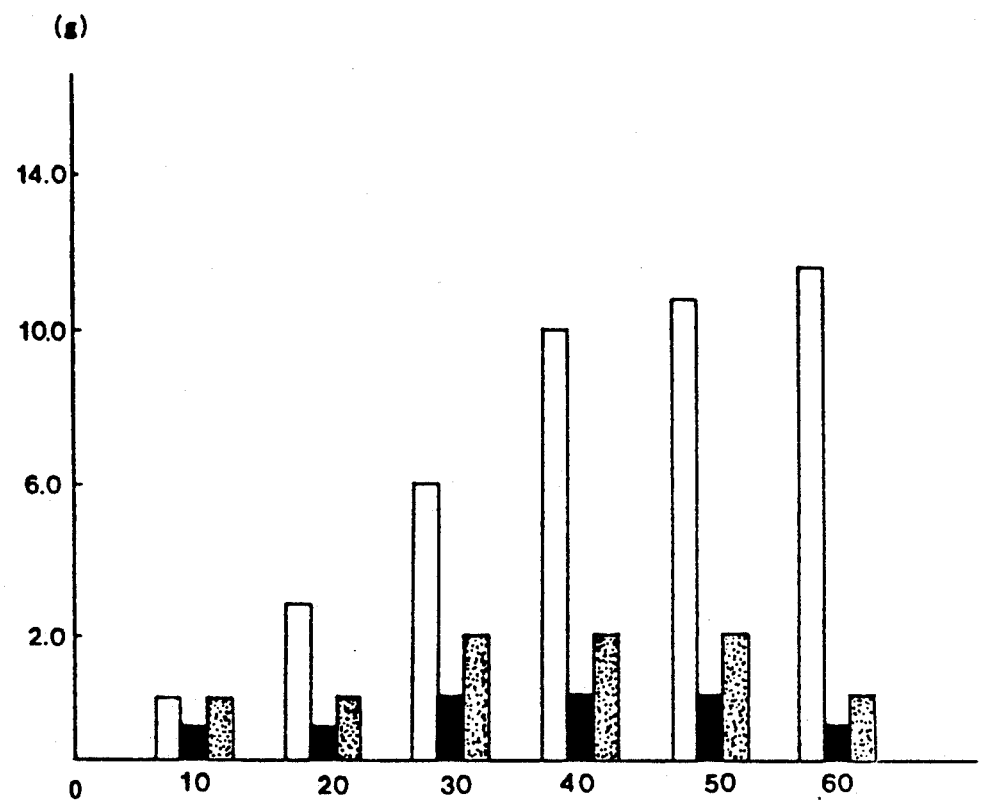
FIG. 9 shows the effect on weight change of the S-180 nodular tumour.
Figure 10:
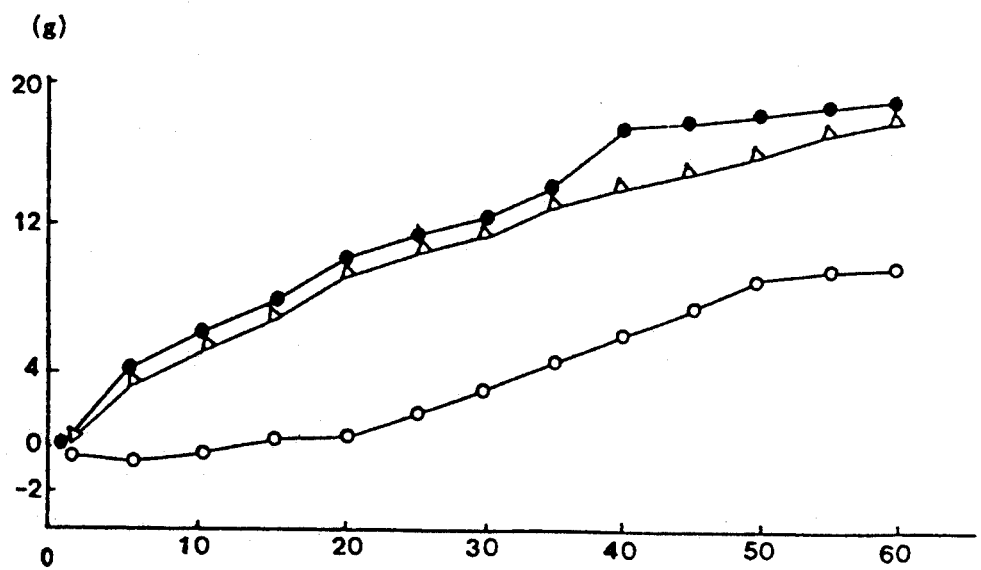
FIG. 10 shows the effect on weight change of mice transplanted with EAC nodular tumour.
Figure 11:
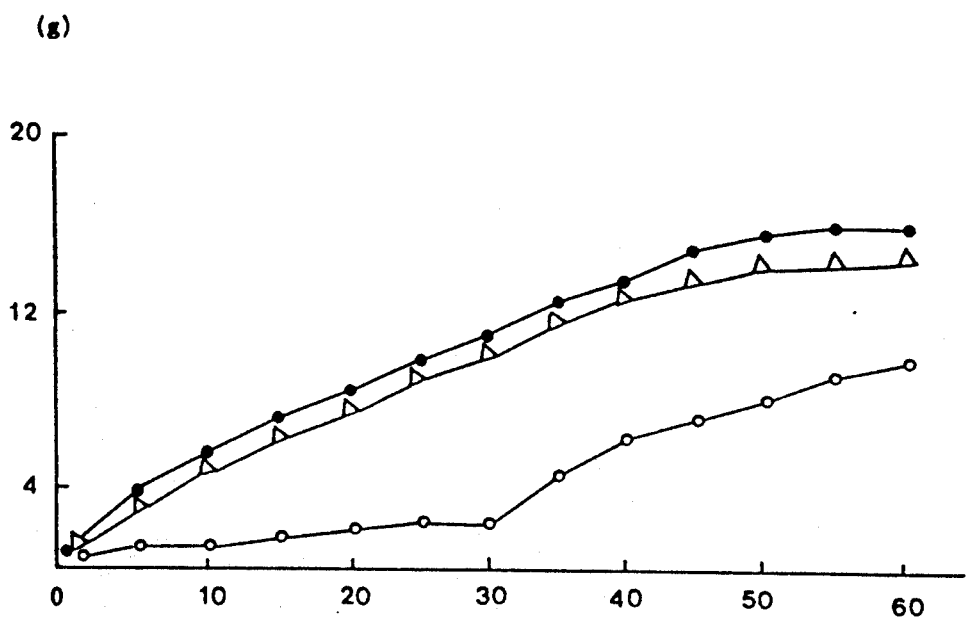
FIG. 11 shows the effect on weight change of mice transplanted with S-180 nodular tumour.

Proliferation-inhibiting figures were calculated again by weight change. FIGS. 8 and 9 show that the proliferated tumour weighed 12 g in the control group, but just below 1 g in the test group. FIGS. 10 and 11 also show that the weight of tumour cells increased remarkably along with their proliferation in the control group, but the weight before inoculation was maintained in the test group until the 30th day.

As illustrated in Table 8, the present extract was intraperitoneally administered continuously until the tumour cells were eradicated and 400 mg/Kg per day was determined to be the most effective (90%) dose among many different dose regimens.

TABLE 8

Antitumor activity of the present extract against nodular tumour
(Results of a 60 day treatment)

| | | inhibition (%) | conclusion |
|------|------|------|------|
| EAC | control | 0 | |
| | treatment 24 hrs after inoculation | 88.9 | Marked Effect |
| | treatment 7 days after inoculation | 72.3 | same as above |
| S-180 | control | 0 | |
| | treatment 24 hrs after inoculation | 90.3 | Marked Effect |
| | treatment 7 days after inoculation | 81.9 | same as above |

Figure 12:
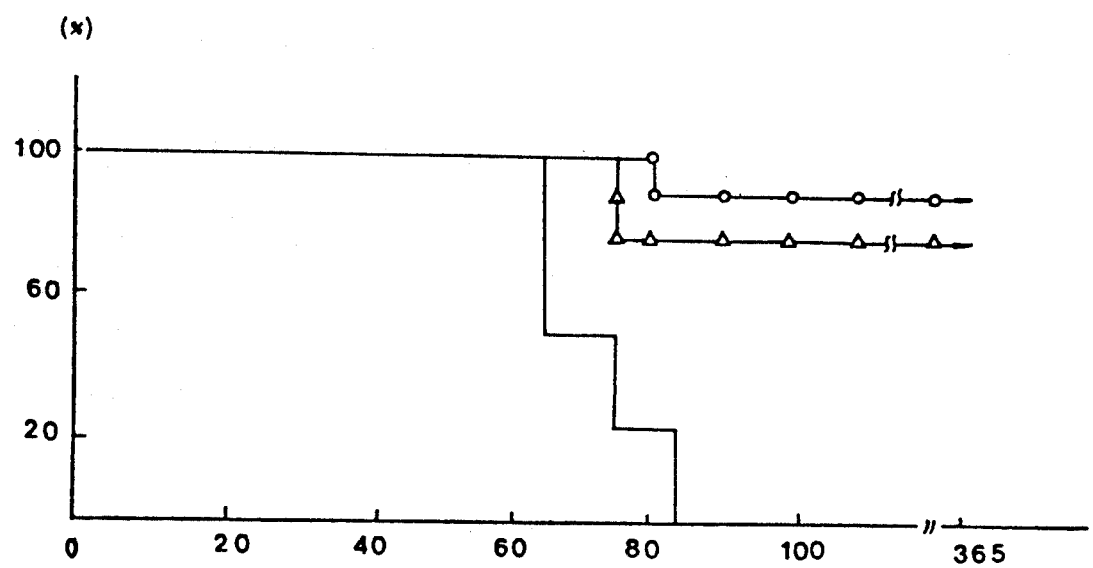
FIG. 12 shows the life prolongation effect against S-180 nodular tumour.
Figure 13:
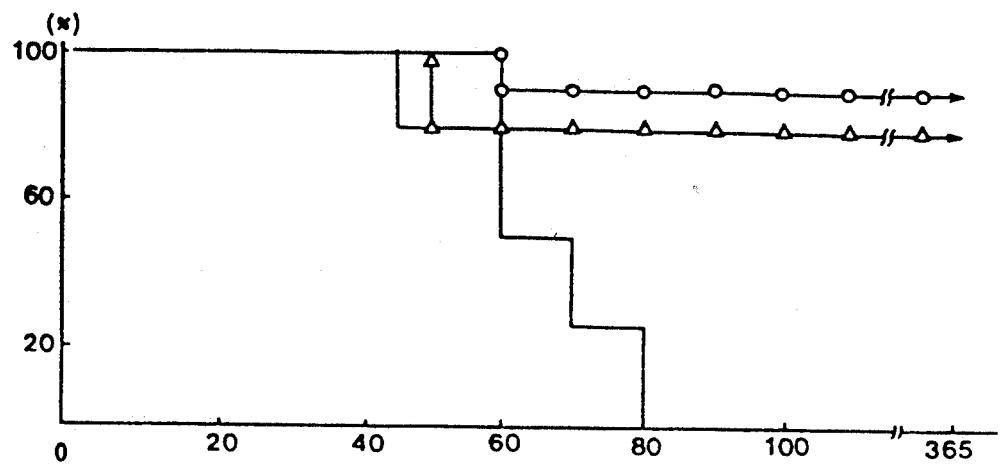
FIG. 13 shows the life prolongation effect against EAC nodular tumour.

As illustrated in FIGS. 12 and 13, the nodular tumour cells were reduced and diminished completely when the present extract was administered continuously and remarkable effects for prolongation of life expectancy of the host were obtained.

(D-3) Effects against tumour SN 36 were investigated.

Figure 14:
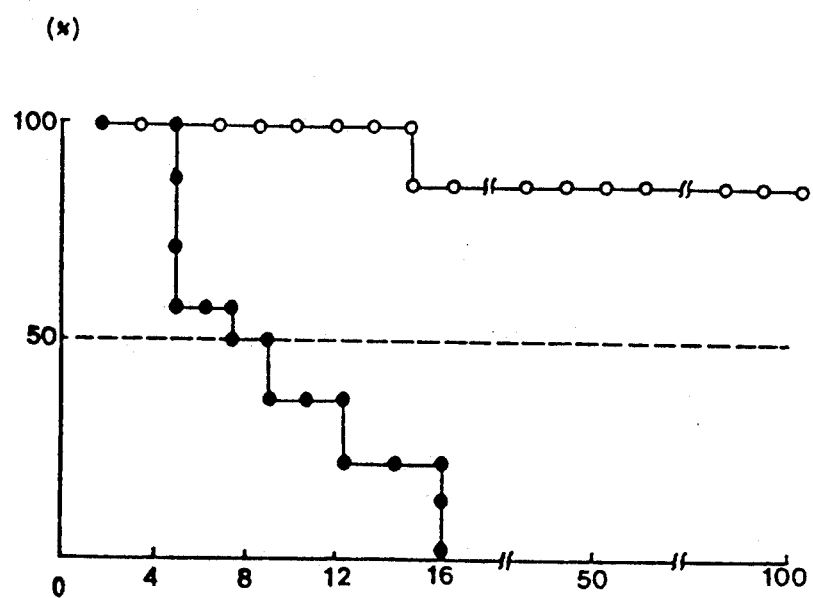
FIG. 14 shows the life prolongation effect against SN36 tumour.

$4 \times 10^6$ of SN 36 tumour cells, a kind of virus-induced lymphatic leukemia, were inoculated into ICR mice (male, $18 \pm 1$ g) through a vein in the tail, and the present extract was administered after 24 hours. The effect of the present extract for prolongation of life expectancy was evaluated. 300 mg/Kg was administered intraperitoneally once a day for 7 days. As shown in FIG. 14, all died from tumour after 4 to 16 days in the control group, but only 20% died in 15 days and the remaining 80% survived up to the 100th day in the test group.

(D-4) Effects against poultry lymphoma were tested.

Lymphoma is one of the prevailing neoplastic leukemias in breeding chickens, which is characterized by the proliferation of immature blood cells. Since the natural prevalence of leukemia is not as yet known, no bench mark to evaluate the drug treatment is available. Accordingly, the experimental animals were taken at random and divided into control and test groups. 100 mg/Kg of the present extract was administered intravenously through a vein in the chicken's wing once per two days for 30 days and the prolongation of life was calculated.

Figure 15:
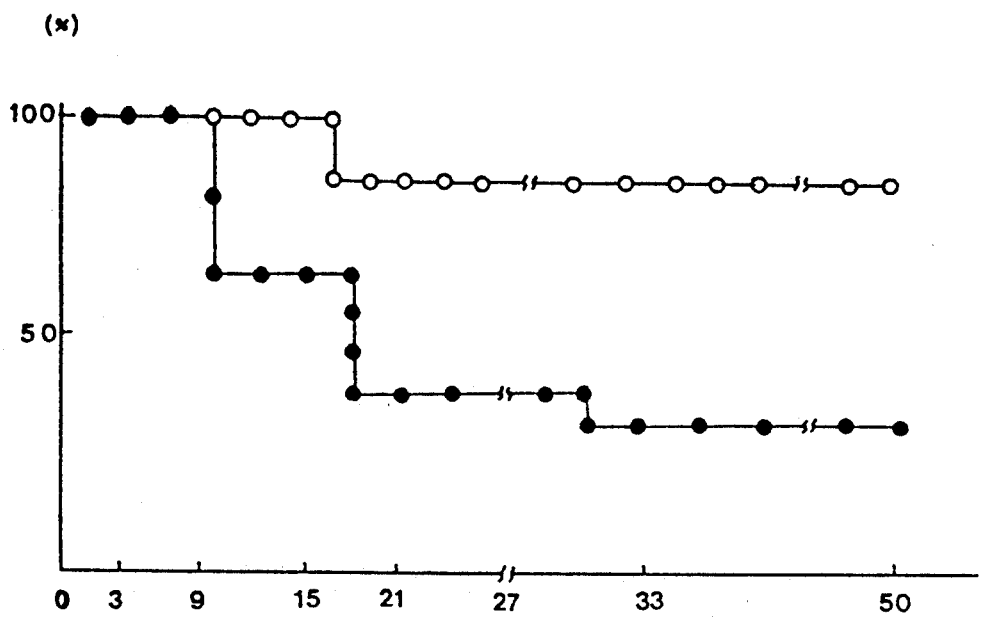
FIG. 15 shows the effect on chicken lymphocytic leukemia (poultry lymphoma)

As illustrated in FIG. 15, 70% of the control group died within 9 to 30 days, but just 15% of the test group died in 15 days and the remaining 85% survived up to the 50th day.

(D-5) Effects against L1210 and P388 tumour were investigated.

L1210 (ATCC CCL 219) and P388 (ATCC CCL 46) cells, the leukemia tumour, are highly lethal. Antitumour activity having 125 to 130% life prolongation effects confirm the present extract as an effective drug for treatment of neoplastic diseases.

$1 \times 10^5$ cells of L1210 tumour were inoculated into BDFI mice (male, $20 \pm 1$) intraperitoneally to induce leukemia, to which the present extract was administered once a day for 15 days 24 hours after the tumour cell inoculation. The mice were divided into four groups and a different dose regimen was administered to each group. The results are shown in Table 9.

TABLE 9

Effect of prolongation of life against L1210.

| cell line | treatment | dose | survival time (day) | survival rate (%) |
|---|---|---|---|---|
| L1210 | control | | 15.5 | 100 |
| | present | 300 mg/Kg | 21.7 | 140 |

TABLE 9-continued

Effect of prolongation of life against L1210.

| cell line | treatment | dose | survival time (day) | survival rate (%) |
|---|---|---|---|---|
| | extract | | | |
| | mitomycin C | 6 mg/Kg | 21 | 135 |
| | mitomycin C + | 6 mg/Kg + | 25.2 | 163 |
| | the extract | 300 mg/Kg | | |

$1 \times 10^6$ cells of P388 were inoculated into BDFI mice intraperitoneally. They were divided into three groups. The same method was applied as in the L1210 test and the results are shown in Table 10.

TABLE 10

Effect of prolongation of life against P388.

| cell line | treatment | dose | survival time (day) | survival rate (%) |
|---|---|---|---|---|
| P388 | control | | 15.8 | 100 |
| | mitomycin C | 6 mg/Kg | 21.6 | 130.4 |
| | mitomycin C + | 6 mg/Kg + | 24 | 150.2 |
| | the extract | 300 mg/Kg | | |

The above results show that the effects of the present extract on L1210 and P388 were almost the same as each other, and the effect of the present extract was excellent when used together with mitomycin C.

(E) Effects in the treatment of viral diseases were investigated.

The proliferation of infectious viruses depends on various factors such as type of virus (DNS or RNA), toxin quantity, sex of the host, etc.

Viral diseases are generally developed by immuno deficiency and other defects of the host, such as children, and are apt to be complicated with neoplastic and renal disorders.

(E-1) Laboratory test.

Established cell lines of DNA and RNA viruses were cultured in serum-free (EAGLE) MEM media (Minimum Essential Media) supplemented with 1-2% fetal bovine serum.

In order to observe the cellular change as an index of virus proliferation, the viruses listed in the following Table 11 were inoculated into cells for culturing in a culture media to which the present extract was added. The dose of the present extract was 1/5, 1/10, 1/20, 1/40 and 1/80 of 50 mg/ml for each test group. Proliferation, damage and other possible morphological changes were observed.

The effectiveness of the present extract against RNA virus was determined to be more excellent than against DNA virus by observing the 50% tissue culture infection dose for each group as shown in Table 11.

TABLE 11

Antiviral activity of the present extract in vitro.

| | | antiviral activity of extract dosage | | | | |
|---|---|---|---|---|---|---|
| virus tested | cell used | 1/5 | 1/10 | 1/20 | 1/40 | 1/80 |
| Aujeszky's | NDBK | Toxic | Toxic | None | None | None |
| Infective bovine rhinotracheitis virus | MDBK | Toxic | Toxic | None | None | None |
| Bovine diarrhea virus | MDBK | Toxic | Toxic | RI 104.0 TCID$_{50}$ | RI 103.0 TCID$_{50}$ | RI 102.0 TCID$_{50}$ |
| Canine parvovirus | primary feline kidney | Toxic | RI 6 HA units | RI 6 HA units | RI 6 HA units | RI 3 HA units |

TABLE 11-continued

Antiviral activity of the present extract in vitro.

| virus tested | cell used | antiviral activity of extract dosage | | | | |
|---|---|---|---|---|---|---|
| | | 1/5 | 1/10 | 1/20 | 1/40 | 1/80 |
| Porcine rotavirus | MA104 | Toxic | RI 102.0 $TCID_{50}$ | RI 102.0 $TCID_{50}$ | None | None |
| Getavirus | Vero | Toxic | RI 3.0 10 $TCID_{50}$ | None | None | None |
| Encephalo-myelocarditis virus | BHK | Toxic | Toxic | Toxic | Toxic | None |
| Transmissible gastroenter-itis | Primary swine testicle | Toxic | Toxic | Toxic | None | None |
| entero-virus | Primary swine testicle | Toxic | Toxic | Toxic | None | None | note)
RI: Reduced Infectivity up to
Toxic: virus toxicity
None: no effectiveness E-2) Effects on Japanese Encephalomyelitis virus were evaluated.

Log 2/0.05 ml of the Japanese encephalomyelitis virus were inoculated into ICR mice and 50 mg/Kg of the present extract were administered intraperitoneally to the mice after 24 hours once a day for 6 days.

Figure 16:
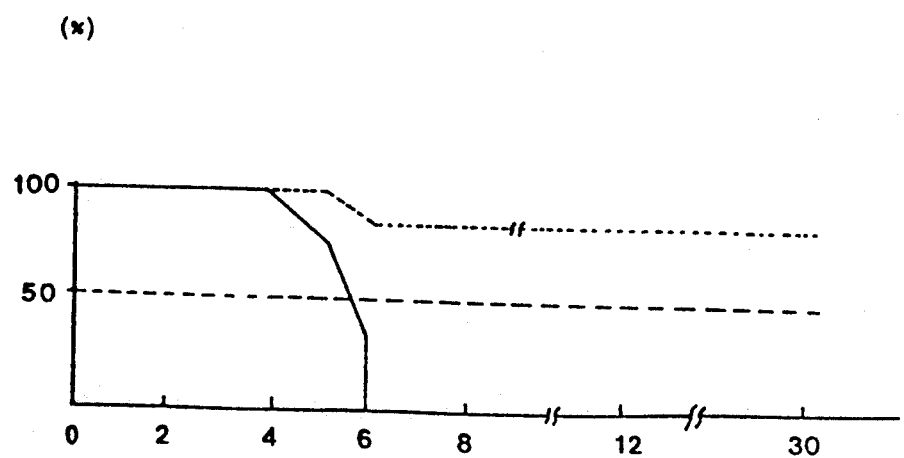
FIG. 16 shows the effect on Japanese encephalomyelitis virus.

As shown in FIG. 16, all died between the 4th and 6th day of neurolysis (particularly in the femur) in the control group, but just 20% died in the same period in the test groups and the remaining 80% survived up to the 30th day.

(E-3) Effect on the treatment of type B hepatitis.

3 mg/Kg of the present extract were administered intramuscularly, at 2-3 day intervals, continuously until Hbe-antibody was detected. The antibody was examined every four weeks by enzyme immune assay(EIA). The standard for determination was as follows:

| | Hbe-antigen/antibody standard by EIA | | | |
|---|---|---|---|---|
| | Hbe Ag | Hbe Ab | negative | reservation |
| HBe Ag (C.I.) | more than 2 1.99-1.0 | | below 1.0 | below 1.9 |
| HBe Ab inhibiting rate | below 30% | more than 70% | below 30% | 30-70% |

C.I.: cut-off index

Figure 17:
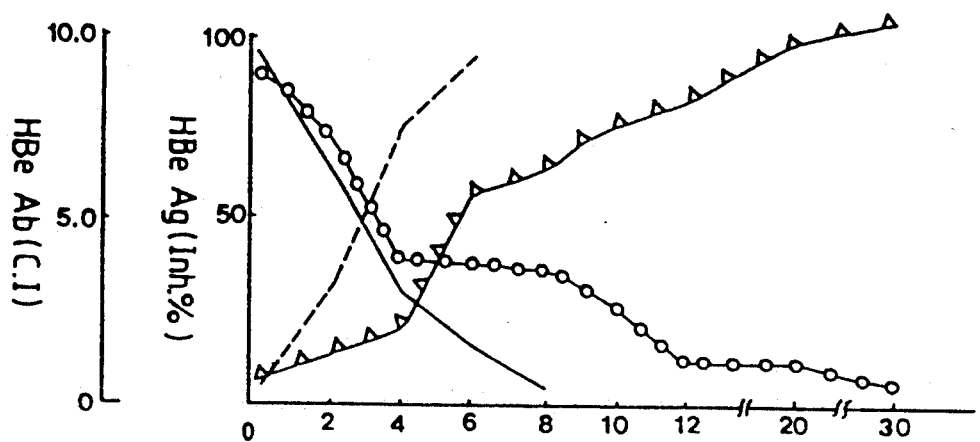
FIG. 17 shows the effect on HBV.
Figure 18:
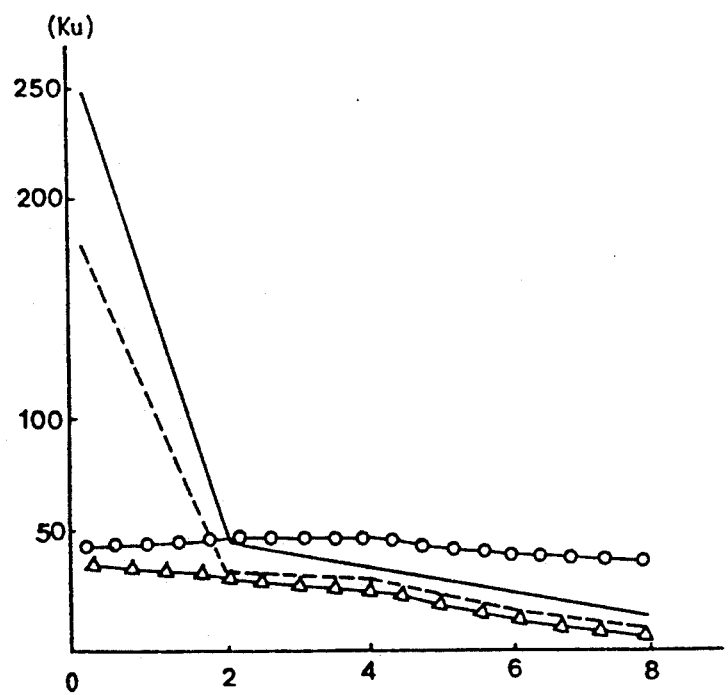
FIG. 18 shows the liver function improvement against HBV.
Figure 19:
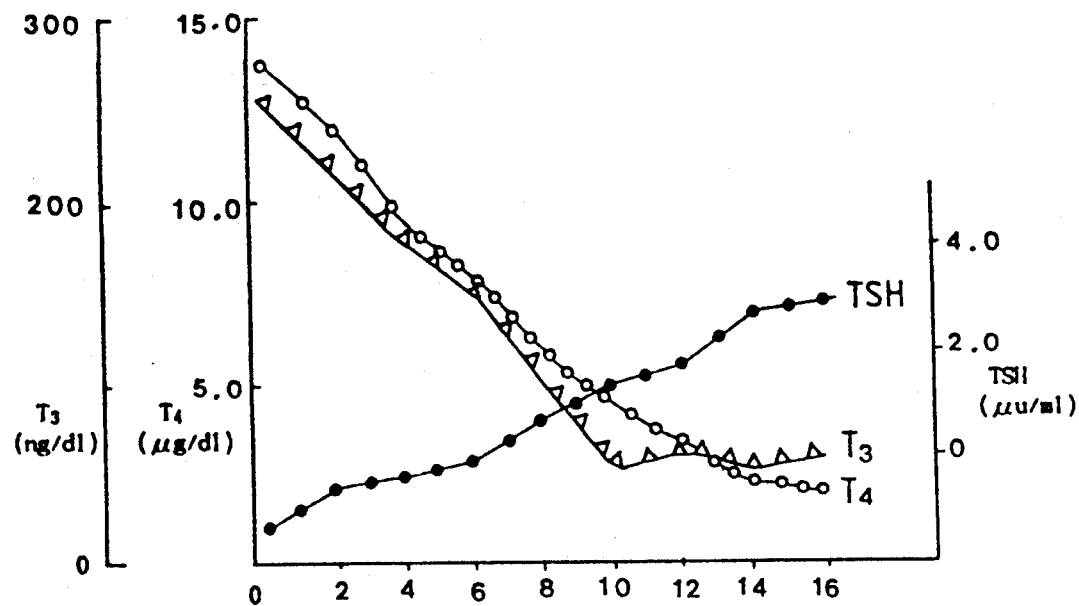
FIG. 19 shows the effect on hyperthyroidism.
Figure 20:
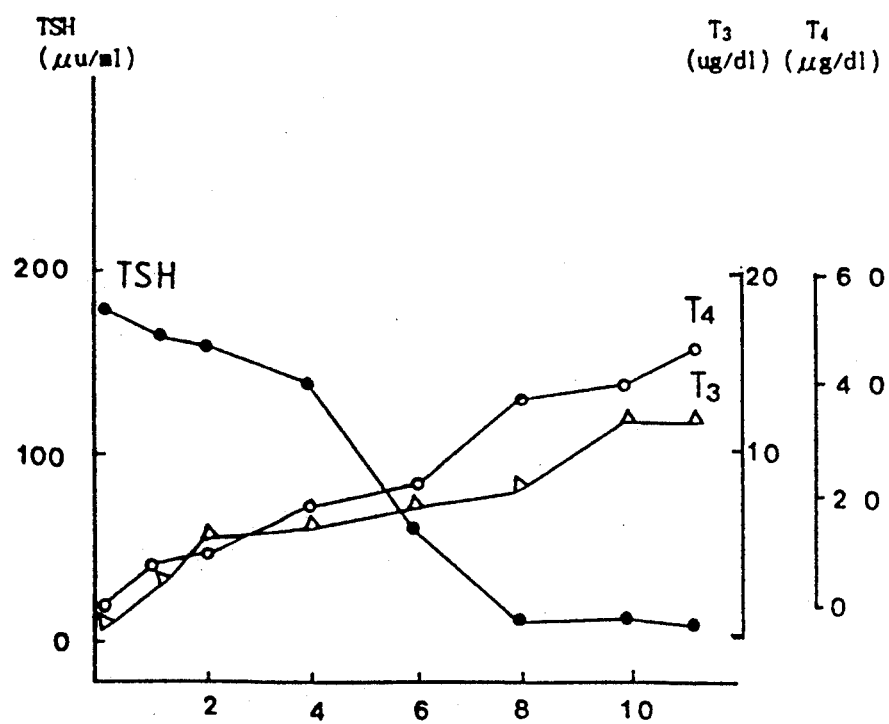
FIG. 20 shows the effect on hypothyroidism.
Figure 21:
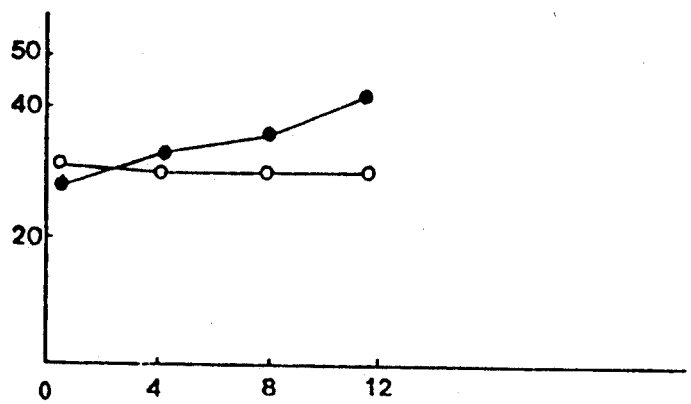
FIG. 21 shows the effect on osteoporosis.

As illustrated in FIGS. 17 and 18, and Tables 12 and 13, a positive antibody reaction was observed more rapidly in acute type B hepatitis than in the chronic form. Cholesterol level was restored to normal rapidly in the acute form also.

TABLE 12

Result of treatment with the present extract on the acute HBV patient.

| | unit | before treatment | after treatment | | | |
|---|---|---|---|---|---|---|
| | | | 4 | 8 | 12 | 48 |
| HBs Ag | (+ −) | (+) | (−) | (−) | (−) | (−) |
| HBs Ab | (+ −) | (−) | (−) | (−) | (−) | (−) |
| Hbe Ag | (+ −) | (+) | (+) | (+) | (−) | (−) |
| HBe Ab | (+ −) | (−) | (−) | (−) | (+) | (+) |
| S-GOT | units | 98 | 42 | 34 | 15.7 | 18.8 |
| S-GPT | units | 137 | 40 | 26 | 21.6 | 20.9 |
| T. protein | g/dl | 7.1 | 7.3 | 7.3 | 7.9 | 6.6 |
| albumin | g/dl | 3.4 | 3.6 | 4.1 | 4.8 | 4.3 |
| globulin | g/dl | 3.7 | 3.7 | 3.2 | 3.1 | 2.3 |

TABLE 12-continued

Result of treatment with the present extract on the acute HBV patient.

| | unit | before treatment | after treatment | | | |
|---|---|---|---|---|---|---|
| | | | 4 | 8 | 12 | 48 |
| bilirubin | mg/dl | 4.8 | 1.01 | 1.01 | 0.76 | 0.74 |
| direct | mg/dl | 1.4 | 0.09 | 0.2 | 0.38 | |
| indirect | mg/dl | | | | | |
| weight | Kg | 47 | 50 | 53 | 56 | 63 |

(subject: M, 26 years)

TABLE 13

Result of treatment with the present extract on the chronic HBV patient.

| | unit | before treatment | after treatment | | | |
|---|---|---|---|---|---|---|
| | | | 4 | 8 | 12 | 48 |
| HBs Ag | (+ −) | (+) | (+) | (+) | (+) | (+) |
| HBs Ab | (+ −) | (−) | (−) | (−) | (−) | (−) |
| Hbe Ag | (+ −) | (+) | (+) | (+) | (−) | (−) |
| HBe Ab | (+ −) | (−) | (−) | (+) | (+) | (+) |
| S-GOT | units | 24.5 | 22.9 | 21.8 | 16.6 | 27.8 |
| S-GPT | units | 57.0 | 36.3 | 38.5 | 27.5 | 37.1 |
| T. protein | g/dl | 6.4 | 7.3 | 7.3 | 7.8 | 7.1 |
| albumin | g/dl | 3.9 | 4.4 | 4.5 | 4.1 | 4.6 |
| bilirubin | mg/dl | 0.74 | 0.72 | 0.76 | 0.71 | 0.71 |

(subject: M, 54 years)

The present extract was assumed to exert therapeutic activity when combined with the following auto-immunizing antibodies and resulted in the normalization of the defense mechanism of the host, the anti-lymphocytic antibody, the antinucleic antibody, the COOMBS antibody, and the smooth muscle antibody.

(F) Effect on the treatment of thyroid disease was investigated.

The thyroid gland, the largest endocrine gland in the human body, secretes thyroidal hormone which plays an important role in health and is one of the essential elements for physical and mental growth. Any disturbances in the gland lead to thyroid diseases.

Hyperthyroidism, the hypersecretion of thyroidal hormone, is characterized by Graves' disease (protruding eyes) and plumer diseases (nodular disseminated leukemic lymphoma). Hypothyroidism, thyroid hypofunction, causes growth inhibition and myxedema.

Thyroid diseases were diagnosed by clinical signs and haematological examination. $T_3$ and $T_4$ levels were restored to normal in four months, and TSH in three months, in the hyperthyroidism group. In the hypothyroidism group, $T_3$ and $T_4$ levels were restored to normal, and TSH was decreased.

In the hyperthyroidism group, the following clinical signs were improved: protruding eyes, myasthenic reaction, irregular menstruation, fatigue, mild fever and neurosis.

In the hypothyroidism group, face edema, hypotension and yellow complexion of the extremities were improved.

(G) Effects on treatment of osteoporosis were investigated.

Osteoporosis is a process of absorption of bone so that the bone tissue becomes unusually porous and fragile. There are many risk factors for osteoporosis: decrease of bone cell function with aging, bone loss due to increased secretion of parathyroid hormone, decreased calcitonin, and decreased estrogen during menopause. Estrogen and progesterone are currently used for treatment, but their effectiveness is not sufficient. Vitamin D and calcium are taken for prevention of osteoporosis.

Sodium fluoride compound has been used to stimulate the osteoblast function in the treatment of osteoporosis, but it is associated with significant side effects. About 30% show adverse effects of nausea and gastric irritation and 10% show rheumatic pain in leg joints. Some possibility of kidney tumour, uterine endometritis and breast cancer by estrogen intake also cannot be excluded.

The present extract appears to stimulate estrogen and calcitonin for activating bone marrow, and to normalize thyroid hormone secretion for enhancing osteoblast resorption, thus resulting in the treatment of osteoporosis.

(G-1) Clinical trial on a severe case whose vertebral density was just 0.332 g/cm$^2$ (29% of normal value), that is, corresponding to the 10th year from each menopause and the inability to walk over ten minutes.

3 mg/Kg of the present extract were administered to the patient once a day for 12 weeks. Estrogen was administered to a patient who showed similar vertebral density as a control.

The vertebral density of the control patient was maintained at 0.341 g/cm$^2$, but increased from 0.332 g/cm$^2$ to 0.476 g/cm$^2$, or by 13%, in the treated patient. The patient who could walk for just ten minutes, could walk for thirty minutes or more after treatment.

It was determined that the present extract is involved in bone metabolism and increases bone density.

(H) Effects on treatment of liver diseases.

Disturbance of bile juice secretion due to liver cell damage is a common symptom of liver diseases. In hepatogenic glycosuria, the decreased liver function impairs the important hormonal function of insulin on glycogen, and results in hyperglycaemia. Disturbed homeostasis of glucose is one of the typical symptoms frequently developed in chronic liver diseases, particularly in liver cirrhosis. In hypoglycaemia, an insulin-like (somatomedin) substance developed by liver tissue damage inhibits glycogenesis and results in hypoglycaemia, which is very common in necrotic hepatitis and liver cancer.

Decreased esterification due to liver cell damage, and elevated bilirubin level (jaundice) due to abnormal bile juice metabolism originating from liver disease, result from acute/chronic hepatitis and/or liver cirrhosis.

For the diagnosis of liver cell damage, GOT/GPT, and total bilirubin level were observed, and as a signal of chronic liver damage, T.T.T. protein fraction and blood glucose were observed.

Figure 22:
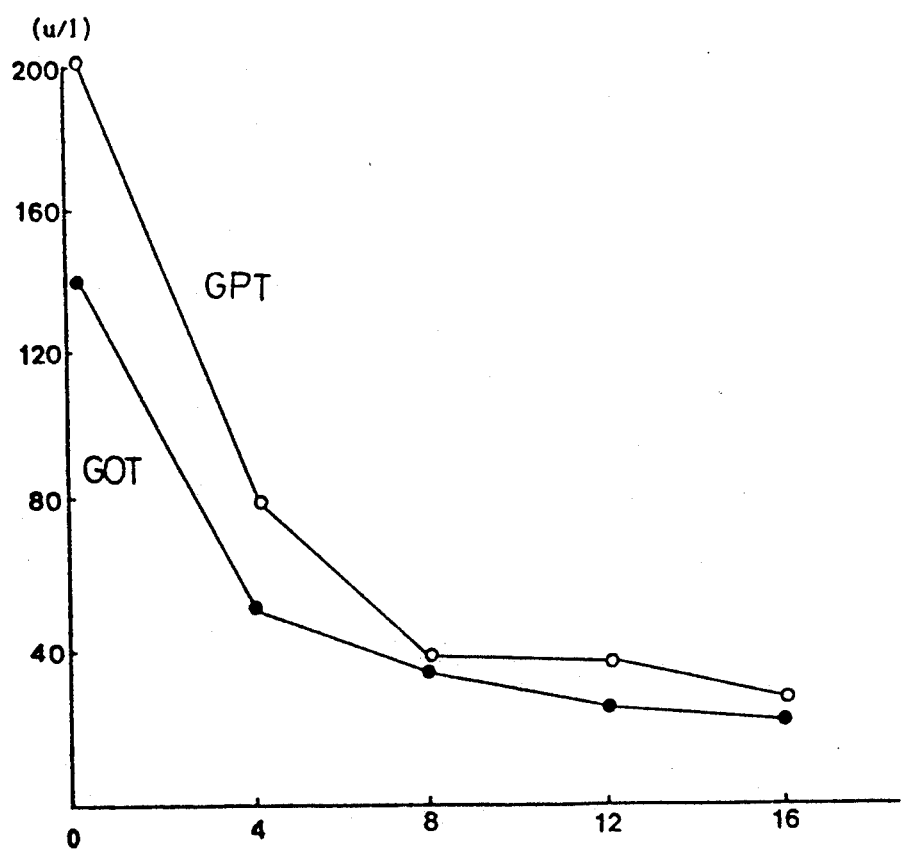
FIG. 22 shows the effect on improvement of GOT/GPT.
Figure 23:
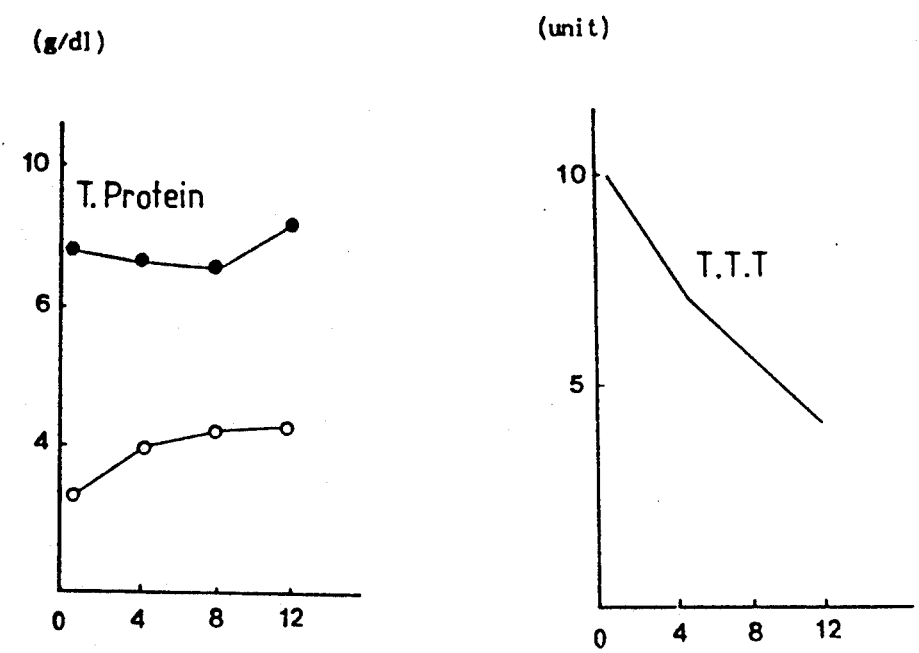
FIG. 23 shows the liver function improvement for hyper- and hypo-glycaemia.
Figure 23:
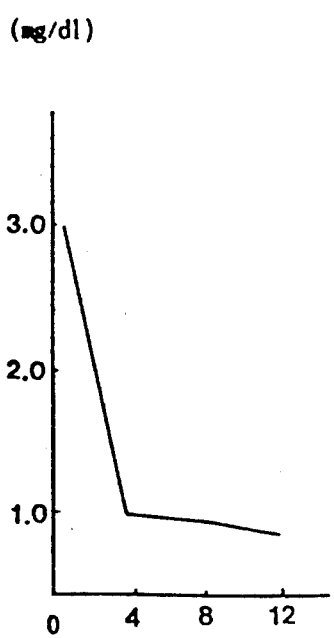
Figure 24:
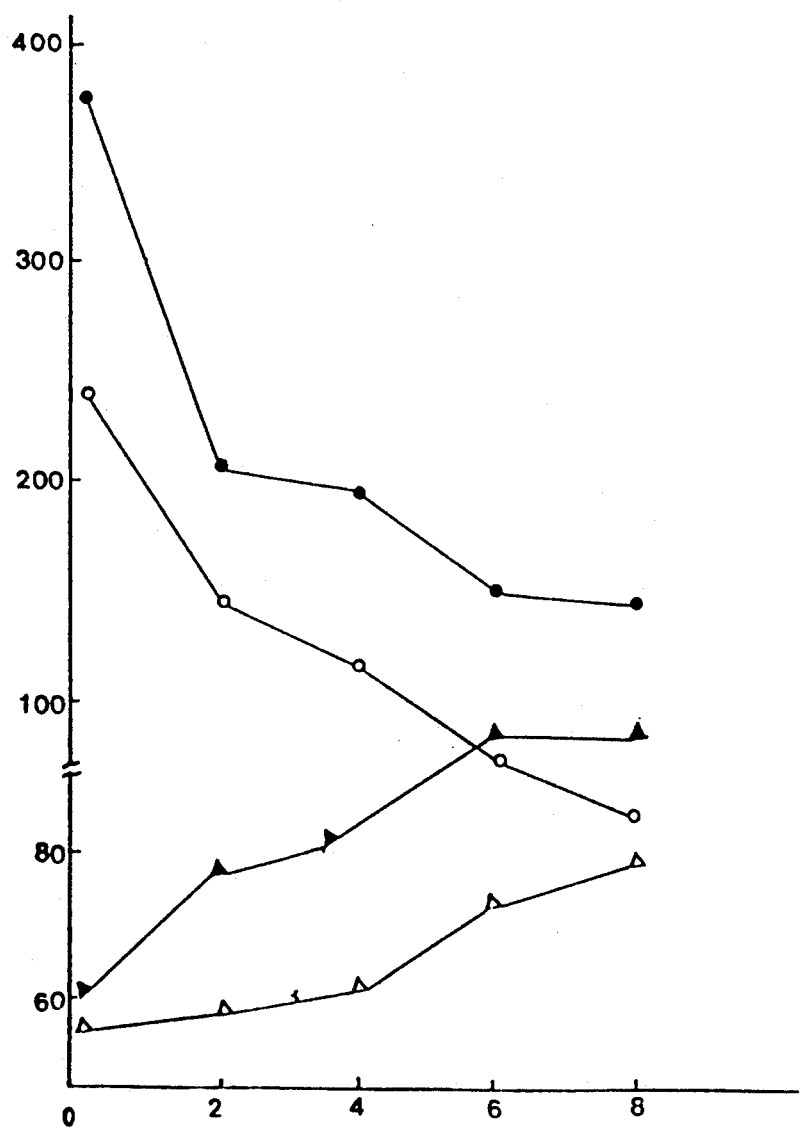
FIG. 24 shows the improvement of hyper- and hypo-glycaemia.

Two to five mg/Kg of the present extract were administered intramuscularly once a day for 12 weeks or 16 weeks at 2–3 day intervals. As shown in FIGS. 22 to 24, GOT/GPT titers were restored to normal in 4 to 8 weeks. A globulin level higher than albumin also was restored to normal in 8 weeks. T.T.T. level was normalized in 12 weeks and bilirubin in four weeks.

The present extract was determined to be effective for the treatment of liver diseases by restoring protein, hormone and bile juice metabolisms of the liver, as well as immune systems, to normal.

What is claimed is:

1. A process for preparing a medicinal extract, comprising adding a first organic solvent to a mixture of bark of genus Phellodendron and defatted seed of genul Croton, stirring the mixture for from 20 to 60 hours at a temperature from room temperature to 50° C. to obtain a residue, extracting the residue with hot water to obtain a water soluble solution, concentrating the water soluble solution under reduced pressure, saturating the concentrated solution with vapor pressure, and removing oil soluble components from the concentrated solution with a second organic solvent.

2. A process as in claim 1, wherein said first and second organic solvents are each selected from the group consisting of an aliphatic alcohol, an aromatic alcohol, a halogenated hydrocarbon having 1 to 6 halogen atoms, a carboxylic ester having a lower alkyl group and mixtures thereof.

3. A process as in claim 1, wherein said first and second organic solvents are selected from the group consisting of chloroform, a lower aliphatic alcohol and mixtures thereof.

4. A process as in claim 3, wherein said lower aliphatic alcohol is ethanol.

5. A process as in claim 1, wherein said removing step comprises separating precipitates from said concentrated and saturated water soluble solution, extracting said concentrated solution with said second organic solvent to obtain a water soluble layer, purifying said water soluble layer, and then lyophilizing said purified water soluble layer to obtain a yellowish brown powder as said extract.

6. An extract produced by the process of claim 1.

7. The extract of claim 6, comprising the following physicochemical properties:
1. Elementary Analysis::
   C: 39–41%, H: 4–6%, O: 45–47%, N: 5–7%
2. HPLC analysis:
   component A (retention time: 2.0 min) : 6–8%
   component B (retention time: 2.8 min) : 6–8%
   component C (retention time: 3.1 min) : 5–7%
   component D (retention time: 5.2 min) : 5–7%
   component E (retention time: 7.1 min) : 33–35%
   component F (retention time: 7.5 min) : 33–35%
   component G (retention time: 8.2 min) : 4–6%
3. UV(KBr):
   339 nm (azo functional group)
   262 nm (substituted benzene functional group)
4. IR spectrum(cm$^{-1}$) : 576, 1301, 1237, 1152, 1509, 1607, 3459, 2926, 3328.

8. A pharmaceutical composition for treating tumours comprising, as an active ingredient, an effective amount of an extract produced by the process of claim 1, and a pharmaceutically acceptable carrier therefor.

* * * * *